United States Patent
Matsumoto et al.

(10) Patent No.: US 11,993,570 B2
(45) Date of Patent: *May 28, 2024

(54) CATIONIC LIPIDS

(71) Applicant: TAKEDA PHARMACEUTICAL COMPANY LIMITED, Osaka (JP)

(72) Inventors: Satoru Matsumoto, Kanagawa (JP); Yoshimasa Omori, Osaka (JP); Masahiro Mineno, Osaka (JP); Yasutaka Hoashi, Kanagawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/900,412

(22) Filed: Aug. 31, 2022

(65) Prior Publication Data
US 2023/0257338 A1    Aug. 17, 2023

Related U.S. Application Data

(63) Continuation of application No. 16/958,244, filed as application No. PCT/JP2018/048054 on Dec. 27, 2018, now abandoned.

(30) Foreign Application Priority Data

Dec. 28, 2017 (JP) ................. 2017-254667

(51) Int. Cl.
| | |
|---|---|
| *C07C 229/12* | (2006.01) |
| *A61K 9/16* | (2006.01) |
| *C07C 69/533* | (2006.01) |
| *C12N 15/113* | (2010.01) |

(52) U.S. Cl.
CPC .......... *C07C 69/533* (2013.01); *A61K 9/1617* (2013.01); *C12N 15/113* (2013.01)

(58) Field of Classification Search
None
See application file for complete search history.

(56) References Cited

U.S. PATENT DOCUMENTS

| | | | |
|---|---|---|---|
| 7,745,651 B2 | 6/2010 | Heyes et al. | |
| 7,982,027 B2 | 7/2011 | MacLachlan et al. | |
| 8,969,543 B2 | 3/2015 | Jeong et al. | |
| 9,371,271 B2 | 6/2016 | Kubo et al. | |
| 2003/0124727 A1 | 7/2003 | Gaucheron et al. | |
| 2004/0043952 A1 | 3/2004 | Niedzinski et al. | |
| 2012/0276209 A1 | 11/2012 | Cullis et al. | |
| 2015/0232883 A1 | 8/2015 | Dahlman et al. | |
| 2015/0343062 A1 | 12/2015 | Kuboyama et al. | |
| 2017/0015994 A1 | 1/2017 | Anderson et al. | |
| 2017/0197903 A1* | 7/2017 | Hoashi ............... | A61K 31/7105 |
| 2018/0353434 A1 | 12/2018 | Hatanaka et al. | |
| 2020/0331841 A1 | 10/2020 | Matsumoto et al. | |
| 2021/0052646 A1 | 2/2021 | Kuwae et al. | |
| 2021/0371854 A1 | 12/2021 | Hotta et al. | |

FOREIGN PATENT DOCUMENTS

| | | |
|---|---|---|
| CN | 104116643 A | 10/2014 |
| CN | 104873976 A | 9/2015 |
| CN | 106536729 A | 3/2017 |
| CN | 106573877 A | 4/2017 |
| CN | 107427531 A | 12/2017 |
| CN | 111542338 A | 8/2020 |
| EP | 2611419 A2 | 7/2013 |
| EP | 3093283 A1 | 11/2016 |

(Continued)

OTHER PUBLICATIONS

Bengtsson et al., Muscle-specific CRISPR/Cas9 dystrophin gene editing ameliorates pathophysiology in a mouse model for Duchenne muscular dystrophy. Nat Commun. Feb. 14, 2017;8:14454.

Li et al., Precise correction of the dystrophin gene in duchenne muscular dystrophy patient induced pluripotent stem cells by TALEN and CRISPR-Cas9. Stem Cell Reports. Jan. 13, 2015;4(1):143-154.

Lim et al., Applications of CRISPR/Cas9 for the Treatment of Duchenne Muscular Dystrophy. J Pers Med. Nov. 24, 2018;8(4):38.

Long et al., Prevention of muscular dystrophy in mice by CRISPR/Cas9-mediated editing of germline DNA. Science. Sep. 5, 2014;345(6201):1184-1188.

Mendell et al., Duchenne muscular dystrophy: CRISPR/Cas9 treatment. Cell Res. May 2016;26(5):513-4.

(Continued)

*Primary Examiner* — Brian Gulledge
(74) *Attorney, Agent, or Firm* — McCarter & English, LLP; David G. Conlin

(57) ABSTRACT

The present invention provides a technique that enables introduction of active ingredients, in particular, nucleic acids, into cells with superior efficiency; and cationic lipids, etc., for use in the technique. The compound or a salt thereof according to the present invention is a compound represented by formula (I) or a salt thereof. In formula (I), n represents an integer of 2 to 5, R represents a linear $C_{1-5}$ alkyl group, a linear $C_{7-11}$ alkenyl group, or a linear $C_{11}$ alkadienyl group, and wavy lines each independently represent a cis-bond or a trans-bond.

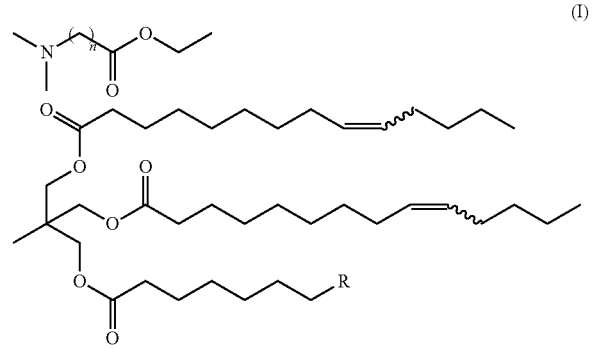

(I)

8 Claims, No Drawings
Specification includes a Sequence Listing.

(56) References Cited

FOREIGN PATENT DOCUMENTS

| | | |
|---|---|---|
| EP | 3178807 A1 | 6/2017 |
| EP | 3733211 A1 | 11/2020 |
| RU | 2573409 C2 | 1/2016 |
| WO | 2003/102150 A2 | 12/2003 |
| WO | 2012/028524 A2 | 3/2012 |
| WO | 2014/197748 A2 | 12/2014 |
| WO | 2016/021683 A1 | 2/2016 |
| WO | 2016/025469 A1 | 2/2016 |
| WO | 2016/153012 A1 | 9/2016 |
| WO | 2016/197133 A1 | 12/2016 |
| WO | 2017/072590 A1 | 5/2017 |

OTHER PUBLICATIONS

Mollanoori et al., Promising therapeutic approaches using CRISPR/Cas9 genome editing technology in the treatment of Duchenne muscular dystrophy. Genes Dis. Jan. 8, 2020;8(2):146-156.

Sharma et al., CRISPR-Cas9: A Preclinical and Clinical Perspective for the Treatment of Human Diseases. Mol Ther. Feb. 3, 2021;29(2):571-586.

Wei et al., Prevention of Muscle Wasting by CRISPR/Cas9-mediated Disruption of Myostatin In Vivo. Mol Ther. Nov. 2016;24(11):1889-1891.

Young et al., A Single CRISPR-Cas9 Deletion Strategy that Targets the Majority of DMD Patients Restores Dystrophin Function in hiPSC-Derived Muscle Cells. Cell Stem Cell. Apr. 7, 2016;18(4):533-40.

Zhang et al., Enhanced CRISPR-Cas9 correction of Duchenne muscular dystrophy in mice by a self-complementary AAV delivery system. Sci Adv. Feb. 19, 2020;6(8):eaay6812.

United States Office Action for U.S. Appl. No. 16/958,006, dated Jan. 10, 2023, 51 pages.

Sun et al., Tailoring non-viral delivery vehicles for transporting genome-editing tools. Sci. China Mater. 2017;60(6):511-5.

Akita et al., "A Neutral Envelope-type Nanoparticle Containing pH-responsive and SS-cleavable Lipid-like Material as a Carrier for Plasmid DNA." Advanced Healthcare Materials Aug. 2013;2(8):1120-5.

Bastin et al., "Salt Selection and Optimisation Procedures for Pharmaceutical New Chemical Entities." Organic Process Research & Development. 2000;4:427-435.

Hirosawa et al., "Cell-type-specific Genome Editing with a MicroRNA-responsive CRISPR-Cas9 Switch." Nucleic Acids Res. Jul. 27, 2017;45(13):e118, 11 pages.

Makita et al., "Advances in Genome Editing Technologies for Treating Muscular Dystrophy." Clinical Calcium. 2017;27(3):67-75.

Tabebordbar et al., "In vivo Gene Editing in Dystrophic Mouse Muscle and Muscle Stem Cells." Science. Jan. 22, 2016;351(6271):407-412.

Yin et al., "Structure-guided Chemical Modification of Guide RNA Enables Potent Non-viral in Vivo Genome Editing." Nature Biotechnology. Dec. 2017;35(12):1179-1188.

Yin et al., "Therapeutic Genome Editing by Combined Viral and Non-viral Delivery of CRISPR System Components in vivo." Nature Biotechnology. Mar. 2016;34(3):328-334.

Zhang et al., "Lipid Nanoparticle-mediated Efficient Delivery of CRISPR/Cas9 for Tumor Therapy." NPG Asia Materials. 2017;9, 8 pages.

European Office Action for Application No. 18894951.5, dated Sep. 30, 2021, 9 pages.

European Office Action for Application No. 18896553.7, dated Sep. 30, 2021, 6 pages.

International Search Report for Application No. PCT/JP2018/048034, Mar. 26, 2019, 6 pages.

International Search Report for Application No. PCT/JP2018/048054, dated Mar. 26, 2019, 4 pages.

Colombian Office Action for Application No. NC2020/0008212 dated Aug. 31, 2022, 8 pages.

Chinese Office Action for Application No. 201880083465.4, dated Aug. 17, 2022, 14 pages.

Taiwan Office Action for Application No. 107147438, dated Sep. 20, 2022, 8 pages.

U.S. Appl. No. 16/958,244, filed Jun. 26, 2020, 2020-0331841, Abandoned.

Cameron, Recent advances in transgenic technology. Mol Biotechnol. Jun. 1997;7(3):253-65.

Gardlik et al., Vectors and delivery systems in gene therapy. Med Sci Monit. Apr. 2005;11(4):RA110-21.

Kappel et al., Regulating gene expression in transgenic animals. Curr Opin Biotechnol. Oct. 1992;3(5):548-53.

Mullins et al., Transgenesis in the rat and larger mammals. J Clin Invest. Apr. 1, 1996;97(7):1557-60.

Phlllips, The challenge of gene therapy and DNA delivery. J Pharm Pharmacol. Sep. 2001;53(9):1169-74.

Wigley et al., Site-specific transgene insertion: an approach. Reprod Ferlil Dev. 1994;6(5):585-8.

\* cited by examiner

CATIONIC LIPIDS

CROSS-REFERENCES TO RELATED APPLICATIONS

This is a continuation application of U.S. patent application Ser. No. 16/958,244, filed on Jun. 26, 2020, which is a National Stage Entry of PCT/JP2018/048054, filed on Dec. 27, 2018, which claims priority to Japanese Patent Application No. 2017-254667, filed on Dec. 28, 2017. The entire contents of each of the aforementioned applications are incorporated herein by reference.

SEQUENCE LISTING

The instant application contains a Sequence Listing which has been submitted electronically in XML format and is hereby incorporated by reference in its entirety. Said XML copy, created on Apr. 27, 2023, is named 136894-00202.xml and is 26,757 bytes in size.

TECHNICAL FIELD

The present invention relates to a cationic lipid that enables introduction of nucleic acids as an active ingredient into many types of cells, tissues, or organs. The present invention further relates to a lipid particle containing the cationic lipid, and a composition containing the lipid particle and a nucleic acid.

BACKGROUND OF INVENTION

Intensive research and development of nucleic acid drugs, which contain a nucleic acid as an active ingredient, have been made in recent years. For example, a number of studies have been conducted for nucleic acid drugs having decomposition effect or function-inhibitory effect on target mRNAs including nucleic acids such as siRNAs, miRNAs, miRNA mimics, and antisense nucleic acids. In addition, studies have been carried out for nucleic acid drugs containing an mRNA or the like encoding a protein of interest to express the protein of interest in cells. In relation to such research and development, techniques to introduce nucleic acids into cells, tissues, or organs with high efficiency have been developed as drug delivery system (DDS) techniques.

Conventionally known as such a DDS technique is such a technique that a nucleic acid and a lipid are mixed to form a complex and cells are allowed to incorporate the nucleic acid via the complex. Conventionally known as lipids for use in formation of the complex are cationic lipids, hydrophilic polymer lipids, helper lipids, and so on. As such cationic lipids, for example, compounds described in prior art documents, as shown below, are known.

Patent Literature 1 describes a compound represented by the following formula or a salt thereof, and so on.

[Formula 1]

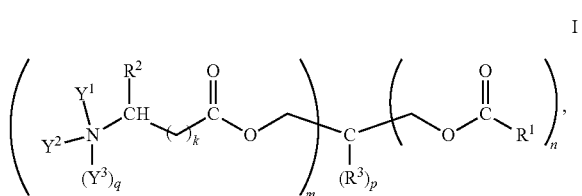

It is specified for the formula that $R^1$ is independently selected from the group consisting of optionally substituted $C_8$-$C_{24}$ alkyl and optionally substituted $C_8$-$C_{24}$ alkenyl; each $R^2$ and $R^3$ is independently selected from the group consisting of hydrogen, optionally substituted $C_1$-$C_8$ alkyl, optionally substituted arylalkyl, and so on; each $Y^1$ and $Y^2$ is independently selected from the group consisting of hydrogen, optionally substituted $C_1$-$C_6$ alkyl, optionally substituted arylalkyl, and so on; each $Y^3$, if present, is independently selected from the group consisting of hydrogen, optionally substituted $C_1$-$C_8$ alkyl, optionally substituted arylalkyl, and so on; m is any integer of 1 to 4; n is any integer of 0 to 3; p is 0 or 1; the sum of m, n, and p is 4; k is any integer of 1 to 5; and q is 0 or 1.

Patent Literature 2 describes a compound represented by the following formula or a salt thereof, and so on.

[Formula 2]

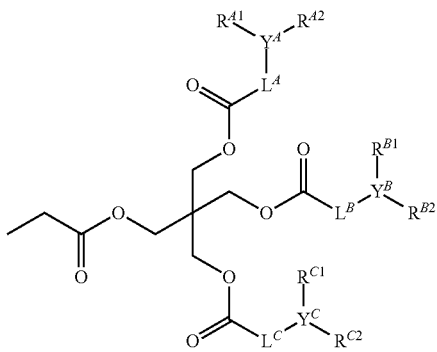

In the formula, W denotes formula —$NR^1R^2$ or formula —$N^*R^3R^4R^5(Z^-)$; $R^1$ and $R^2$ denote, each independently, a $C_{1-4}$ alkyl group or hydrogen atom; $R^3$, $R^4$, and $R^5$ denote, each independently, a $C_{1-4}$ alkyl group; $Z^-$ denotes a negative ion; X denotes a $C_{1-6}$ alkylene group which may be substituted; $Y^A$, $Y^B$ and $Y^C$ denote, each independently, a methine group which may be substituted; $L^A$, $L^B$, and $L^C$ denote, each independently, a methylene group which may be substituted or a bond; $R^{A1}$, $R^{A2}$, $R^{B1}$, $R^{B2}$, $R^{C1}$, and $R^{C2}$ denote, each independently, a $C_{4-10}$ alkyl group which may be substituted.

CITATION LIST

Patent Literature

Patent Literature 1: International Publication No. WO 2003/102150

Patent Literature 2: International Publication No. WO 2016/021683

SUMMARY OF INVENTION

Technical Problem

Cationic lipids that enable introduction of nucleic acids into cells with high efficiency are expected to contribute to creation of nucleic acid drugs that are superior in terms of manifestation of drug action, safety (low toxicity), and so on and exhibit therapeutically superior effect. Cationic lipids that enable introduction of nucleic acids into various cells are expected to enable creation of nucleic acid drugs for diseases that occur in various tissues. Currently, however, no cationic lipid that sufficiently satisfies those requirements has been found.

An object of the present invention is to provide a technique that enables introduction of nucleic acids into cells with superior efficiency; and cationic lipids, etc., for use in the technique. An object of the present invention from another viewpoint is to provide a technique that enables introduction of nucleic acids into various cells; and compounds, etc., for use in the technique.

Solution to Problem

The present inventors have diligently examined to solve the problem and found that the problem is successfully solved by using a compound represented by the formula below or a salt thereof, thus completing the present invention.

Specifically, the present invention relates at least to the followings.

[1] A compound represented by formula (I):

[Formula 3]

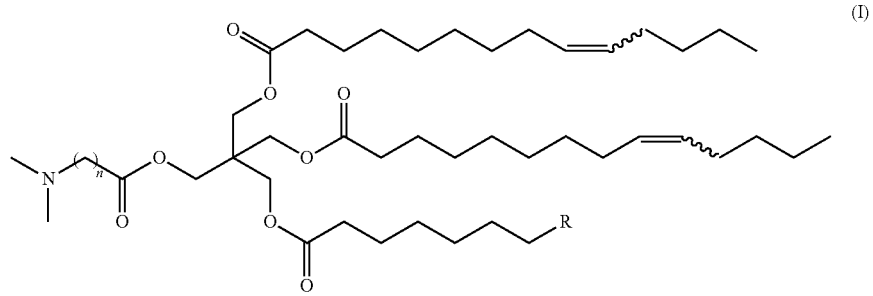

(I)

wherein
n represents an integer of 2 to 5,
R represents a linear $C_{1-5}$ alkyl group, a linear $C_{7-11}$ alkenyl group, or a linear $C_{11}$ alkadienyl group, and wavy lines each independently represent a cis-bond or a trans-bond, or a salt thereof.

[2] 3-((4-(Dimethylamino)butanoyl)oxy)-2,2-bis(((9Z)-tetradec-9-enoyloxy)methyl)propyl (9Z)-tetradec-9-enoate or a salt thereof.

[3] 3-((5-(Dimethylamino)pentanoyl)oxy)-2,2-bis(((9Z)-tetradec-9-enoyloxy)methyl)propyl (9Z)-tetradec-9-enoate or a salt thereof.

[4] 3-((6-(Dimethylamino)hexanoyl)oxy)-2,2-bis(((9Z)-tetradec-9-enoyloxy)methyl)propyl (9Z)-tetradec-9-enoate or a salt thereof.

[5] A lipid particle containing the compound or a salt thereof according to item 1.

[6] A composition for nucleic acid introduction containing a nucleic acid and the lipid particle according to item 5.

[7] The composition according to item 6, wherein the nucleic acid is an RNA.

[7a] The composition according to item 6, wherein the nucleic acid is a DNA.

[8] The composition according to item 7, wherein the RNA is an mRNA or an siRNA.

Herein, "the compound represented by formula (I)" is occasionally referred to as "compound (I)". "The compound represented by formula (I) or a salt thereof" is occasionally called "the compound of the present invention". A "lipid particle containing the compound represented by formula (I) or a salt thereof (the compound of the present invention)" is occasionally called "the lipid particle of the present invention". A "composition for nucleic acid introduction containing a nucleic acid and the lipid particle of the present invention" is occasionally called "the composition of the present invention".

Advantageous Effects of Invention

The present invention enables introduction of nucleic acids into cells, tissues, or organs with superior efficiency. The present invention enables introduction of nucleic acids into various types of cells, tissues, or organs (e.g., cancer cells). The present invention enables acquisition of drugs or reagents for research to introduce a nucleic acid into various types of cells, tissues, or organs. Moreover, if a nucleic acid is introduced into cells, a tissue, or an organ through the present invention, the efficiency of manifestation of the activity (e.g., drug action) possessed by the nucleic acid is high.

DETAILED DESCRIPTION OF INVENTION

Now, definitions of substituents used herein will be described in detail. Substituents have the following definitions, unless otherwise specified.

Examples of the "linear $C_{1-5}$ alkyl group" herein include methyl, ethyl, propyl, butyl, and pentyl.

Examples of the "linear $C_{7-11}$ alkenyl group" herein include 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, and 10-undecenyl. While each of these linear $C_{7-11}$ alkenyl groups has one carbon-carbon double bond, and hence the carbon-carbon double bond can form a cis-structure and a trans-structure, the carbon-carbon double bond may form any of the structures.

Examples of the "linear $C_{11}$ alkadienyl group" herein include 1,3-undecadienyl, 1,4-undecadienyl, 1,5-undecadienyl, 1,6-undecadienyl, 1,7-undecadienyl, 1,8-undecadienyl, 1,9-undecadienyl, 1,10-undecadienyl, 2,4-undecadienyl, 2,5-undecadienyl, 2,6-undecadienyl, 2,7-undecadienyl, 2,8-undecadienyl, 2,9-undecadienyl, 2,10-undecadienyl, 3,5-undecadienyl, 3,6-undecadienyl, 3,7-undecadienyl, 3,8-undecadienyl, 3,9-undecadienyl, 3,10- undecadienyl, 4,6-undecadienyl, 4,7-undecadienyl, 4,8-undecadienyl, 4,9-undecadienyl, 4,10-undecadienyl, 5,7-undecadienyl, 5,8-undecadienyl, 5,9-undecadienyl, 5,10-undecadienyl, 6,8-undecadienyl, 6,9-undecadienyl, 6,10-undecadienyl, 7,9-undecadienyl, 7,10-undecadienyl, and 8,10-undecadienyl. While each of these linear $C_{11}$ alkadienyl groups has two carbon-carbon double bonds, and hence the carbon-carbon double bonds can each independently form a cis-structure and a trans-structure, each carbon-carbon double bond may form any of the structures.

Preferred examples of n and the wavy lines in formula (I) are as follows.

n is preferably an integer of 3 to 5, and more preferably 3.

The wave lines are preferably each a cis-bond.

Specific preferred examples of compound (I) are as follows.

Compound (A): such a compound that n is an integer of 3 to 5, R is a linear C7.11 alkenyl group in a cis-structure, and the wavy lines are each a cis-bond.

Compound (B): such a compound that n is 4, R is a linear $C_{11}$ alkadienyl group in which two carbon-carbon double bonds each form a cis-structure, and the wavy lines are each a cis-bond.

Compound (C): such a compound that n is 2 or 3, R is a linear $C_{1-5}$ alkyl group, and the wavy lines are each a cis-bond.

Specific, more preferred examples of compound (I) are as follows.

Compound (A1): such a compound that n is an integer of 3 to 5, R is 5-heptenyl, 7-nonenyl, or 9-undecenyl in the cis-structure, and the wavy lines are each a cis-bond.

Compound (B1): such a compound that n is 4, R is 2,5-undecadienyl in which two carbon-carbon double bonds each form a cis-structure, and the wavy lines are each a cis-bond.

Compound (C1): such a compound that n is 2 or 3, R is methyl, propyl, or pentyl, and the wavy lines are each a cis-bond.

The salt of compound (I) is preferably a pharmacologically acceptable salt, and examples thereof include salts with an inorganic base, salts with an organic base, salts with an inorganic acid, salts with an organic acid, and salts with a basic or acidic amino acid.

Preferred examples of salts with an inorganic base include alkali metal salts such as sodium salts and potassium salts; alkali earth metal salts such as calcium salts and magnesium salts; aluminum salts; and ammonium salts. Preferred are sodium salts, potassium salts, calcium salts, and magnesium salts, and more preferred are sodium salts and potassium salts.

Preferred examples of salts with an organic base include salts with trimethylamine, triethylamine, pyridine, picoline, ethanolamine, diethanolamine, triethanolamine, trometh-amine[tris(hydroxymethyl)methylamine], tert-butylamine, cyclohexylamine, benzylamine, dicyclohexylamine, and N,N-dibenzylethylenediamine.

Preferred examples of salts with an inorganic acid include salts with hydrofluoric acid, hydrochloric acid, hydrobromic acid, hydroiodic acid, nitric acid, sulfuric acid, and phosphoric acid. Preferred are salts with hydrochloric acid and salts with phosphoric acid.

Preferred examples of salts with an organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, and p-toluenesulfonic acid.

Preferred examples of salts with a basic amino acid include salts with arginine, lysine, and ornithine.

Preferred examples of salts with an acidic amino acid include salts with aspartic acid and glutamic acid.

In the present invention, the compound of the present invention may be used as a cationic lipid. The cationic lipid can form a complex with a plurality of molecules in a solvent or dispersion medium. The complex may contain an additional component in addition to the compound of the present invention. Examples of the additional component include an additional lipid component and a nucleic acid.

Examples of the additional lipid component include structural lipids capable of constituting a lipid particle. For such a structural lipid, for example, at least one selected from the group consisting of the following may be used:

sterols (e.g., cholesterol, cholesteryl ester, cholesteryl hemisuccinate);

phospholipids (e.g., phosphatidylcholine (e.g., dipalmitoylphosphatidylcholine, distearoylphosphatidylcholine, lysophosphatidylcholine, dioleoylphosphatidylcholine, palmitoyloleoylphosphatidylcholine, dilinolenoylphosphatidylcholine, MC-1010 (NOF CORPORATION), MC-2020 (NOF CORPORATION), MC-4040 (NOF CORPORATION)), phosphatidylserine (e.g., dipalmitoylphosphatidylserine, distearoylphosphatidylserine, dioleoylphosphatidylserine, palmitoyloleoylphosphatidylserine), phosphatidylethanolamine (e.g., dipalmitoylphosphatidylethanolamine, distearoylphosphatidylethanolamine, dioleoylphosphatidylethanolamine, palmitoyloleoylphosphatidylethanolamine, lysophosphatidylethanolamine), phosphatidylinositol, phosphatidic acid); and polyethylene glycol lipids (PEG lipids) (e.g., PEG-DAA, PEG-DAG, PEG-phospholipid cunjugate, PEG-Cer, PEG-cholesterol, PEG-C-DOMG, 2KPEG-CMG, GM-020 (NOF CORPORATION), GS-020 (NOF CORPORATION), GS-050 (NOF CORPORATION)).

In the present invention, it is preferred to use all of the three, namely, a sterol (in particular, cholesterol), a phospholipid (in particular, phosphatidylcholine), and a polyethylene glycol lipid, as the structural lipid.

The ratio between the compound of the present invention and the structural lipid in the mixed lipid component constituting the lipid particle of the present invention may be appropriately controlled according to the purpose or use. For example, the ratio of the structural lipid is typically 0.008 to 4 mol and preferably 0.4 to 1.5 mol per mole of the compound of the present invention. In another definition of ratios in the mixed lipid component, the amount of the compound of the present invention is typically 1 to 4 mol, that of the sterol is typically 0 to 3 mol, that of the phospholipid is typically 0 to 2 mol, and that of the polyethylene glycol lipid is typically 0 to 1 mol. In a more preferred embodiment with use of a mixture of the compound of the present invention and additional lipid components, with respect to ratios, the amount of the compound of the present invention is 1 to 1.5 mol, that of the sterol is 0 to 1.25 mol, that of the phospholipid is 0 to 0.5 mol, and that of the polyethylene glycol lipid is 0 to 0.125 mol.

The compound of the present invention may be used for producing the lipid particle of the present invention. The lipid particle of the present invention refers to the complex described above but containing no nucleic acid. The shape of the lipid particle of the present invention is not limited to a particular shape, and the scope includes a complex in which the compound of the present invention and so on assemble to form a sphere; a complex in which the compound of the present invention and so on assemble without forming a particular shape; a complex in which the compound of the present invention and so on dissolve in a solvent; and a complex in which the compound of the present invention and so on homogeneously or heterogeneously disperse in a dispersion medium.

The lipid particle of the present invention (e.g., a lipid particle composed of the compound of the present invention and structural lipids other than the compound) may be used, for example, for producing the composition of the present invention containing the lipid particle and a nucleic acid (in particular, a nucleic acid as a substance useful for pharmaceutical applications or applications for research). The composition of the present invention may be used as a drug or a reagent. It is preferred for the composition of the present invention that the lipid particle encapsulate a nucleic acid in a ratio as high as possible (i.e., in a high encapsulation ratio).

The "nucleic acid" may be any molecule in which molecules of nucleotide or molecules having functions equivalent to those of the nucleotide are polymerized, and examples thereof include RNA, which is a polymer of ribonucleotide; DNA, which is a polymer of deoxyribonucleotide; a polymer of a mixture of ribonucleotide and deoxyribonucleotide; and a nucleotide polymer including a nucleotide analog. Further, the nucleic acid may be a nucleotide polymer including a nucleic acid derivative. The nucleic acid may be a single-stranded nucleic acid or a double-stranded nucleic acid. The concept of the double-stranded nucleic acid encompasses a double-stranded nucleic acid such that one strand hybridizes with the other strand under stringent conditions.

The nucleotide analog may be any molecule obtained by modifying ribonucleotide, deoxyribonucleotide, RNA, or DNA to improve nuclease resistance, to stabilize, to enhance affinity with a complementary-strand nucleic acid or to enhance cell permeability as compared with RNA or DNA, or for visualization. The nucleotide analog may be a naturally-occurring molecule or a non-natural molecule, and examples thereof include a sugar-modified nucleotide analog and a phosphodiester bond-modified nucleotide analog.

The sugar-modified nucleotide analog may be any one obtained by addition of or substitution with a substance having an arbitrary chemical structure for a part or the whole of the chemical structure of the sugar of a nucleotide. Specific examples thereof include a nucleotide analog substituted with 2'-O-methylribose, a nucleotide analog substituted with 2'-O-propylribose, a nucleotide analog substituted with 2'-methoxyethoxyribose, a nucleotide analog substituted with 2'-O-methoxyethylribose, a nucleotide analog substituted with 2'-O-[2-(guanidinium)ethyl]ribose, a nucleotide analog substituted with 2'-O-fluororibose, a crosslinked artificial nucleic acid provided with two cyclic structures by introducing a crosslinked structure to the sugar moiety (Bridged Nucleic Acid) (BNA), more specifically, a locked artificial nucleic acid in which the oxygen atom at position 2' and the carbon atom at position 4' are crosslinked via methylene (Locked Nucleic Acid) (LNA) and an ethylene-crosslinked artificial nucleic acid (Ethylene bridged nucleic acid) (ENA) [Nucleic Acid Research, 32, e175 (2004)], further, a peptide nucleic acid (PNA) [Acc. Chem. Res., 32, 624 (1999)], an oxypeptide nucleic acid (OPNA) [J. Am. Chem. Soc., 123, 4653 (2001)], and a peptide ribonucleic acid (PRNA) [J. Am. Chem. Soc., 122, 6900 (2000)].

The phosphodiester bond-modified nucleotide analog may be any one obtained by addition of or substitution with an arbitrary chemical substance for a part or the whole of the chemical structure of the phosphodiester bond of a nucleotide. Specific examples thereof include a nucleotide analog substituted with a phosphorothioate bond and a nucleotide analog substituted with an N3'-P5' phosphoramidate bond [Saibo Kogaku (in Japanese, translated title: Cell Engineering), 16, 1463-1473 (1997)] [RNAi and Antisense Strategies, KODANSHA LTD. (2005)].

The nucleic acid derivative may be any molecule obtained by adding to a nucleic acid another chemical substance to improve nuclease resistance, to stabilize, to enhance affinity with a complementary-strand nucleic acid, or to enhance cell permeability as compared with the nucleic acid, or for visualization. Specific examples thereof include a derivative with 5'-polyamine added, a derivative with cholesterol added, a derivative with steroid added, a derivative with bile acid added, a derivative with vitamin added, a derivative with Cy5 added, a derivative with Cy3 added, a derivative with 6-FAM added, and a derivative with biotin added.

The nucleic acid in the present invention is not limited to a particular nucleic acid, and may be a nucleic acid, for example, for the purpose of ameliorating a disease, a symptom, a disorder, or sickness, and mitigating a disease, a symptom, a disorder, or pathological condition or preventing the onset thereof (herein, occasionally referred to as "treatment or the like of a disease"), or a nucleic acid for regulating expression of a desired protein that is useful for research, even though the protein does not contribute to treatment or the like of a disease.

Genes or polynucleotides related to diseases (herein, occasionally referred to as "disease-related genes") are available, for example, from McKusick-Nathans Institute of Genetic Medicine, Johns Hopkins University (Baltimore, Md.) and National Center for Biotechnology Information, National Library of Medicine (Bethesda, Md.).

Specific examples of the nucleic acid in the present invention include siRNAs, shRNAs, miRNAs, miRNA mimics, antisense nucleic acids, ribozymes, mRNAs, decoy nucleic acids, aptamers, plasmid DNAs, Cosmid DNAs, and BAC DNAs. The nucleic acid is preferably an RNA such as an siRNA and an mRNA or an analog or derivative obtained by artificially modifying an RNA.

In the present invention, the "siRNA" refers to a double-stranded RNA or relative thereof consisting of 10 to 30 nucleotides, preferably of 15 to 25 nucleotides, and including complementary sequences. The siRNA includes protruding nucleotides preferably of one to three nucleotides, more preferably of two nucleotides, at the 3-end. The moiety of complementary sequences may be completely complementary or include non-complementary nucleotides, but preferably are completely complementary.

The siRNA in the present invention is not limited to a particular siRNA, and, for example, an siRNA for knockdown of gene expression against a disease-related gene may be used. A disease-related gene refers to any gene or polynucleotide generating a transcription or translation product at an abnormal level or in an abnormal form in cells derived from tissue of a patient, as compared with tissue or cells from a disease-free control. For the siRNA in the present invention, an siRNA to regulate expression of a desired protein useful for research may be used.

In the present invention, the "mRNA" refers to an RNA including a nucleotide sequence that can be translated into a protein. The mRNA in the present invention is not limited to a particular mRNA and may be any mRNA capable of expressing a desired protein in cells. The mRNA is preferably an mRNA useful for pharmaceutical applications (e.g., applications of disease treatment) and/or applications for research, and examples of such mRNAs include an mRNA to express a marker protein such as luciferase in cells.

The disease is not limited to a particular disease, and examples of the disease include diseases listed below. Contents in each "( )" are examples of the corresponding disease-related gene, except for the case that specific disease examples are listed. Another example of the nucleic acid in the present invention is a nucleic acid that regulates the expression level of any of those disease-related genes (or a protein encoded by the disease-related gene).

(1) Diseases of blood system [anaemia (CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT), bare lymphocyte syndrome (TAPBP, TPSN, TAP2, ABCB3, PSF2, RING11, MHC2TA, C2TA, RFX5), hemorrhagic diseases (TBXA2R, P2RX1, P2X1), factor H and factor H-like 1 deficiencies (HF1, CFH, HUS), factor V and factor VIII deficiencies (MCFD2), factor VII deficiency (F7), factor X deficiency (F10), factor XI deficiency (F11), factor XII deficiency (F12, HAF), factor XIIIA deficiency (F13A1, F13A), factor XIIIB deficiency (F13B), Fanconi's anaemia(FANCA, FACA, FA1, FA, FAA, FAAP95, FAAP90, FLJ34064, FANCB, FANCC, FACC, BRCA2, FANCD1, FANCD2, FANCD, FACD, FAD, FACE, FACE, FANCF, XRCC9, FANCG, BRIP1, BACH1, FANCJ, PHF9, FANCL, FANCM, KIAA1596), haemophagocytic lymphohistiocytosis (PRF1, HPLH2, UNC13D, MUNC13-4, HPLH3, HLH3, FHL3), haemophilia A (F8, F8C, HEMA), haemophilia B (F9, HEMB), haemorrhagic disorders (PI, ATT, F5), leucocyte deficiency (ITGB2, CD18, LCAMB, LAD, EIF2B1, EIF2BA, EIF2B2, EIF2B3, EIF2B5, LVWM, CACH, CLE, EIF2B4), sickle cell anaemia (HBB), thalassaemia (HBA2, HBB, HBD, LCRB, HBA1), and so on];

(2) inflammatory/immunologic diseases [AIDS (KIR3DL1, NKAT3, NKB1, AMB11, KIR3DS1, IFNG, CXCL12, SDF1), autoimmune lymphoproliferative syndrome (TNFRSF6, APTI, FAS, CD95, ALPS1A), combined immunodeficiency (IL2RG, SCIDX1, SCIDX, IMD4), HIV infection (CCL5, SCYA5, D17S135E, TCP228, IL10, CSIF, CMKBR2, CCR2, DMKBR5, CCCKR5, CCR5), immunodeficiency (CD3E, CD3G, AICDA, AID, HIGM2, TNFRSF5, CD40, UNG, DGU, HIGM4, TNFSF5, CD40LG, HIGM1, IGM, FOXP3, IPEX, ARD, XPID, PIDX, TNFRSF14B, TACI), inflammation (I10, IL-1, IL-13, IL-17, IL-23, CTLA4), severe combined immunodeficiency (JAK3, JAKL, DCLRE1C, ATREMIS, SCIDA, RAG1, RAG2, ADA, PTPRC, CD45, LCA, IL7R, CD3D, T3D, IL2RG, SCIDX1, SCIDX, IMD4), rheumatoid arthritis, psoriasis, inflammatory bowel diseases (e.g., Crohn's disease, ulcerative colitis), Sjogren's syndrome, Behcet's disease, multiple sclerosis, systemic lupus erythematosus, lupus nephritis, discoid lupus erythematosus, Castleman's disease, ankylosing spondylitis, polymyositis, dermatomyositis, polyarteritis nodosa, mixed connective tissue disease, dermatosclerosis, lupus profundus, chronic thyroiditis, Graves' disease, autoimmune gastritis, type I and type II diabetes mellitus, autoimmune haemolytic anaemia, autoimmune neutropenia, thrombocytopenia, atopic dermatitis, chronic active hepatitis, myasthenia gravis, graft-versus-host disease, Addison's disease, abnormal immune response, arthritis, dermatitis, radiodermatitis, primary biliary cirrhosis, and so on];

(3) metabolic/liver/kidney diseases [amyloid neuropathy (TTR, PALB), amyloidosis (APOA1, APP, AAA, CVAP, AD1, GSN, FGA, LYZ, TTR, PALB), non-alcoholic steatohepatitis and hepatic fibrosis (COL1A1), cirrhosis (KRT18, KRT8, CIRHIA, NAIC, TEX292, KIAA1988), cystic fibrosis (CFTR, ABCC7, CF, MRP7), glycogen storage disease (SLC2A2, GLUT2, G6PC, G6PT, G6PT1, GAA, LAMP2, LAMPB, AGL, GDE, GBE1, GYS2, PYGL, PFKM), hepatocellular adenoma (TCFl, HFN1A, MODY3), hepatic failure (SCOD1, SCO1), hepatic lipase deficiency (LIPC), hepatoblastoma (CTNNB1, PDFGRL, PDGRL, PRLTS, AXIN1, AXIN, TP53, P53, LFS1, IGF2R, MPRI, MET, CASP8, MCH5), medullary cystic kidney disease (UMOD, HNFJ, FJHN, MCKD2, ADMCKD2), phenylketonuria (PAH, PKU1, QDPR, DHPR, PTS), multicystic kidney and liver diseases (FCYT, PKHD1, APRKD, PDK1, PDK2, PDK4, PDKTS, PRKCSH, G19P1, PCLD, SEC63), and so on];

(4) nervous system diseases (ALS (SOD1, ALS2, STEX, FUS, TARDBP, VEGF), Alzheimer's disease (APP, AAA, CVAP, AD1, APOE, AD2, PSEN2, AD4, STM2, APBB2, FE65L1, NOS3, PLAU, URK, ACE, DCP1, ACE1, MPO, PACIP1, PAXIP1L, PTIP, A2M, BLMH, BMH, PSEN1, AD3), autism (BZRAP1, MDGA2, GLO1, MECP2, RTT, PPMX, MRX16, MRX79, NLGN3, NLGN4, KIAA1260, AUTSX2), fragile X syndrome (FMR2, FXR1, FXR2, mGLUR5), Huntington's disease (HD, IT15, PRNP, PRIP, JPH3, JP3, HDL2, TBP, SCA17), Parkinson's disease (NR4A2, NURR1, NOT, TINUR, SNCAIP, TBP, SCA17, SNCA, NACP, PARK1, PARK4, DJ1, DBH, NDUFV2), Rett syndrome (MECP2, RTT, PPMX, MRX16, MRX79, CDKL5, STK9), schizophrenia (GSK3, 5-HTT, COMT, DRD, SLC6A3, DAOA, DTNBP1), secretase-related disorder (APH-1), and so on];

(5) eye diseases [age-related macular degeneration (Abcr, Ccl2, cp, Timp3, cathepsin D, Vldlr, Ccr2), cataract (CRYAA, CRYA1, CRYBB2, CRYB2, PITX3, BFSP2, CP49, CP47, PAX6, AN2, MGDA, CRYBA1, CRYB1, CRYGC, CRYG3, CCL, LIM2, MP19, CRYGD, CRYG4, BSFP2, CP49, CP47, HSF4, CTM, MIP, AQPO, CRYAB, CRYA2, CTPP2, CRYBB1, CRYGD, CRYG4, CRYA1, GJA8, CX50, CAE1, GJA3, CX46, CZP3, CAE3, CCM1, CAM, KRIT1), corneal opacity (APOA1, TGFB1, CSD2, CDGG1, CSD, BIGH3, CDG2, TASTD2, TROP2, M1S1, VSX1, RINX, PPCD, PPD, KTCN, COL8A2, FECD, PPCD2, PIP5K3, CFD), congenital hereditary corneal plana (KERA, CNA2), glaucoma (MYOC, TIGR, GLC1A, JOAG, GPOA, OPTN, GLC1E, FIP2, HYPL, NRP, CYP1B1, GLC3A, OPA1, NTG, NPG, CYP1B1, GLC3A), Leber's congenital amaurosis (CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3), macular dystrophy (ELOVL4, ADMD, STGD2, STGD3, RDS, RP7, PRPH2, PRPH, AVMD, AOFMD, VMD2), and so on]; and (6) neoplastic diseases [malignant tumor, neovascular glaucoma, infantile hemangioma, multiple myeloma, chronic sarcoma, metastatic melanoma, Kaposi's sarcoma, angioproliferation, cachexia, metastasis or the like of breast cancer, cancer (e.g., colorectal cancer (e.g., familial colorectal cancer, hereditary nonpolyposis colorectal cancer, gastrointestinal stromal tumor), lung cancer (e.g., non-small cell lung cancer, small cell lung cancer, malignant mesothelioma), mesothelioma, pancreatic cancer (e.g., pancreatic ductal carcinoma), gastric cancer (e.g., papillary adenocarcinoma, mucinous adenocarcinoma, adenosquamous cell carcinoma), breast cancer (e.g., invasive ductal breast carcinoma, noninvasive ductal breast carcinoma, inflammatory breast carcinoma), ovarian cancer (e.g., epithelial ovarian cancer, extragonadal germ cell tumor, ovarian germ cell tumor, low-grade ovarian tumor), prostate cancer (e.g., hormone-dependent prostate cancer, hormone-independent prostate cancer), liver cancer (e.g., primary liver cancer, extrahepatic bile duct cancer), thyroid cancer (e.g., medullary thyroid cancer), kidney cancer (e.g., renal cell carcinoma, transitional cell carcinoma of renal pelvis and ureter), uterine cancer, brain tumor (e.g., pineal astrocytoma, pilocytic astrocytoma, diffuse astrocytoma, anaplastic astrocytoma), melanoma, sarcoma, bladder cancer, hematological cancer or the like including multiple myeloma, pituitary adenoma, glioma, acoustic neurinoma, retinal sarcoma, pharyngeal cancer, laryngeal cancer, tongue cancer, thymoma, esophageal carcinoma, duodenal cancer, colon cancer, rectal cancer, hepatocellular carcinoma, pancreatic endocrine tumor, bile duct cancer, gallbladder cancer, penile cancer, ureteric cancer, testicular tumor, vulvar carcinoma, cervix cancer, corpus uteri carcinoma, uterine sarcoma, trophoblastic disease, vaginal cancer, skin cancer, mycosis fungoides, basalioma, soft part sarcoma, malignant lymphoma, Hodgkin's disease, myelodysplastic syndrome, adult T-cell leukemia, chronic myeloproliferative disease, pancreatic endocrine tumor, fibrous histiocytoma, leiomyosarcoma, rhabdomyosarcoma, carcinoma of unknown primary), leukaemia (e.g., acute leukaemia (e.g., acute lymphocytic leukaemia, acute myeloid leukaemia), chronic leukaemia (e.g., chronic lymphocytic leukaemia, chronic myeloid leukaemia), myelodysplastic syndrome), uterine sarcoma (e.g., uterine mesodermal mixed tumor, uterine leiomyosarcoma, endometrial stromal tumor), myelofibrosis, and so on].

The composition of the present invention as a drug may be produced by using a method known in the art of drug formulation with a pharmaceutically acceptable carrier. Examples of the dosage form of the drug include formulations for parenteral administration (e.g., a liquid such as an injection) blended with a conventional auxiliary such as a buffering agent and/or a stabilizer; and formulations for topical administration, such as an ointment, a cream, a liquid, and a plaster, blended with a conventional pharmaceutical carrier.

The composition of the present invention may be used for introduction of an active ingredient into various types of cells, tissues, or organs. Examples of cells to which the composition of the present invention may be applied include mesenchymal stem cells, neural stem cells, skin stem cells, splenocytes, nerve cells, glial cells, pancreatic B cells, bone marrow cells, mesangial cells, Langerhans cells, epidermal cells, epithelial cells, endothelial cells, fibroblasts, fiber cells, muscle cells (e.g., skeletal muscle cells, cardiac muscle cells, myoblasts, muscle satellite cells, smooth muscle cells), fat cells, blood cells (e.g., macrophages, T cells, B cells, natural killer cells, mast cells, leukocytes, neutrophils, basophils, eosinophils, monocytes, megakaryocytes, hematopoietic stem cells), synoviocytes, chondrocytes, osteocytes, osteoblasts, osteoclasts, mammary cells, hepatocytes or stromal cells, ova, spermatids, or precursor cells capable of inducing differentiation into these cells, stem cells (e.g., including induced pluripotent stem cells (iPS cells), embryonic stem cells (ES cells)), primordial germ cells, oocytes, and fertilized ova. Examples of tissues or organs to which the composition of the present invention may be applied include all tissues or organs in which the above cells are present, for example, brain, sites of brain (e.g., olfactory bulb, amygdala, basal ganglion, hippocampus, thalamus, hypothalamus, subthalamic nucleus, cerebral cortex, medulla oblongata, cerebellum, occipital lobe, frontal lobe, temporal lobe, putamen, caudate nucleus, callosum, substantia nigra), spinal cord, pituitary gland, stomach, pancreas, kidney, liver, gonad, thyroid, gallbladder, bone marrow, adrenal gland, skin, lung, digestive tract (e.g., large intestine, small intestine), blood vessel, heart, thymus, spleen, submandibular gland, peripheral blood, peripheral blood cells, prostate, placenta, uterus, bones, joints, and muscles (e.g., skeletal muscle, smooth muscle, cardiac muscle). Those cells, tissues, or organs may be cancer cells, cancer tissues, or the like that have undergone canceration.

The composition of the present invention is particularly superior in efficiency to introduce a nucleic acid into cancer cells.

The compound, the lipid particle, and the composition of the present invention are stable and have low toxicity and can be safely used. In using the composition of the present invention in vivo, or using the composition as a drug, the composition is suitably administered to a subject (e.g., a human or a non-human mammal (preferably, a human)) so that an effective amount of the nucleic acid can be delivered to targeted cells.

In using the composition of the present invention in vivo, or using the composition as a drug, the composition can be orally or parenterally (e.g., local, rectal, or intravenous administration) administered in a safe manner in the form of a pharmaceutical formulation such as tablets (including sugar-coated tablets, film-coated tablets, sublingual tablets, orally disintegrating tablets), powders, granules, capsules (including soft capsules, microcapsules), liquids, troches, syrups, emulsions, suspensions, injections (e.g., subcutaneous injections, intravenous injections, intramuscular injections, intraperitoneal injections), topical formulations (e.g., formulations for nasal administration, transdermal formulations, ointments), suppositories (e.g., rectal suppositories, vaginal suppositories), pellets, nasal formulations, pulmonary formulations (inhalations), and infusions. Each formulation may be a controlled-release formulation such as a fast-release formulation and a sustained-release formulation (e.g., a sustained-release microcapsule).

Now, a method for producing the compound of the present invention will be described.

Raw materials and reagents used in each step of the production method below, and the resulting compound may each form a salt. Examples of such salts are the same as the above-mentioned salts for the compound of the present invention.

When a compound obtained in each step is a free compound, the compound may be converted into an intended salt by using a known method. Conversely, when a compound obtained in each step is a salt, the compound may be converted into a free form or another intended salt by using a known method.

A compound obtained in each step may be used for the subsequent reaction directly as a reaction solution, or a crude product may be obtained therefrom and used for the subsequent reaction. Alternatively, a compound obtained in each step may be isolated and/or purified from a reaction mixture according to a conventional method using a separation means such as concentration, crystallization, recrystallization, distillation, solvent extraction, fractional distillation, and chromatography.

If a compound as a raw material or reagent in each step is commercially available, the commercially available product may be directly used.

Reaction time for reaction in each step, which may vary depending on reagents and solvents to be used, is typically 1 minute to 48 hours, and preferably 10 minutes to 8 hours, unless otherwise specified.

Reaction temperature for reaction in each step, which may vary depending on reagents and solvents to be used, is typically −78° C. to 300° C., and preferably −78° C. to 150° C., unless otherwise specified.

Pressure for reaction in each step, which may vary depending on reagents and solvents to be used, is typically 1 atm to 20 atm, and preferably 1 atm to 3 atm, unless otherwise specified.

A microwave synthesis apparatus such as an Initiator produced by Biotage is occasionally used in reaction in a step. The reaction temperature, which may vary depending on reagents and solvents to be used, is typically room temperature to 300° C., preferably room temperature to 250° C., and more preferably 50° C. to 250° C., unless otherwise specified. The reaction time, which may vary depending on reagents and solvents to be used, is typically 1 minute to 48 hours, and preferably 1 minute to 8 hours, unless otherwise specified.

In reaction in each step, a reagent is used in an amount of 0.5 equivalents to 20 equivalents, preferably in an amount of 0.8 equivalents to 5 equivalents, to the amount of a substrate, unless otherwise specified. When a reagent is used as a catalyst, the reagent is used in an amount of 0.001 equivalents to 1 equivalent, preferably in an amount of 0.01 equivalents to 0.2 equivalents, to the amount of a substrate, unless otherwise specified. If a reagent serves as a reaction solvent in combination with its own role, the reagent is used in an amount as solvent.

In reaction in each step, the reaction is performed without solvent, or in an appropriate solvent dissolving or suspending reactants therein, unless otherwise specified. Examples of the solvent include solvents described in Examples and the following solvents.

Alcohols: methanol, ethanol, isopropanol, isobutanol, tert-butyl alcohol, 2-methoxyethanol, and so on;
  ethers: diethyl ether, diisopropyl ether, diphenyl ether, tetrahydrofuran, 1,2-dimethoxyethane, and so on;
  aromatic hydrocarbons: chlorobenzene, toluene, xylene, and so on;
  saturated hydrocarbons: cyclohexane, hexane, heptane, and so on;
  amides: N,N-dimethylformamide, N-methylpyrrolidone, and so on;
  halogenated hydrocarbons: dichloromethane, carbon tetrachloride, and so on;
  nitriles: acetonitrile and so on;
  sulfoxides: dimethylsulfoxide and so on;
  aromatic organic bases: pyridine and so on;
  acid anhydride: acetic anhydride and so on;
  organic acids: formic acid, acetic acid, trifluoroacetic acid, and so on;
  inorganic acids: hydrochloric acid, sulfuric acid, and so on;
  esters: ethyl acetate, isopropyl acetate, and so on;
  ketones: acetone, methyl ethyl ketone, and so on; and water.

Two or more of these solvents may be mixed for use with an appropriate ratio.

When a base is used in reaction in each step, for example, any of bases listed below or bases described in Examples is used.

Inorganic bases: sodium hydroxide, potassium hydroxide, magnesium hydroxide, and so on;
  basic salts: sodium carbonate, calcium carbonate, sodium hydrogen carbonate, and so on;
  organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine, and so on;
  metal alkoxides: sodium ethoxide, potassium tert-butoxide, sodium tert-butoxide, and so on;
  alkali metal hydrides: sodium hydride and so on;
  metal amides: sodium amide, lithium diisopropylamide, lithium hexamethyldisilazide, and so on; and
  organolithiums: n-butyllithium, sec-butyllithium, and so on.

When an acid or an acidic catalyst is used in reaction in each step, for example, any of acids and acidic catalysts listed below and acids and acidic catalysts described in Examples is used.

Inorganic acids: hydrochloric acid, sulfuric acid, nitric acid, hydrobromic acid, phosphoric acid, and so on;
  organic acids: acetic acid, trifluoroacetic acid, citric acid, p-toluenesulfonic acid, 10-camphorsulfonic acid, and so on; and
  Lewis acids: boron trifluoride-diethyl ether complex, zinc iodide, anhydrous aluminum chloride, anhydrous zinc chloride, anhydrous iron chloride, and so on.

Unless otherwise specified, reaction in each step is performed in accordance with a known method such as a method described in The Fifth Series of Experimental Chemistry, Vol. 13 to 19 (The Chemical Society of Japan (ed.)); Shin Jikken Kagaku Koza (in Japanese, translated title: New Experimental Chemistry), Vol. 14 and 15 (The Chemical Society of Japan (ed.)); Seimitsu Yuki Kagaku (in Japanese, translated title: Precise Organic Chemistry, original title: Reaktionen und Synthesen im organisch-chemischen Praktikum und Forschungslaboratorium) Revised 2nd Edition (L. F. Tietze, Th. Eicher, Nankodo Co., Ltd.); Organic Name Reaction; The Reaction Mechanism and Essence Revised Edition (TOGO, Hideo, KODANSHA LTD.); ORGANIC SYNTHESES Collective Volume I to VII (John Wiley & Sons Inc.); Modern Organic Synthesis in the Laboratory A Collection of Standard Experimental Procedures (Jie Jack Li, Oxford University Pres); Comprehensive Heterocyclic Chemistry III, Vol. 1 to Vol. 14 (Elsevier Japan K.K.); Strategic Applications of Named Reactions in Organic Synthesis (translation supervisor: TOMIOKA, Kiyoshi, publisher: Kagaku-Dojin Publishing Company, INC.); Comprehensive Organic Transformations (VCH Publishers Inc.) (1989); or the like, or in accordance with a method described in Examples.

Protection or deprotection reaction for a functional group in each step is performed in accordance with a known method such as a method described in "Protective Groups in Organic Synthesis, 4th Ed." (Theodora W. Greene, Peter G. M. Wuts) published by Wiley-Interscience Publication, 2007; "Protecting Groups 3rd Ed." (P. J. Kocienski) published by Thieme Medical Publishers, 2004; or the like, or in accordance with a method described in Examples.

Examples of protective groups for a hydroxy group of alcohols or the like and phenolic hydroxy groups include ether-type protective groups such as methoxymethyl ether, benzyl ether, p-methoxybenzyl ether, t-butyldimethylsilyl ether, t-butyldiphenylsilyl ether, and tetrahydropyranyl ether; carboxylate-type protective groups such as acetate; sulfonate-type esters such as methanesulfonate; and carbonate-type protective groups such as t-butylcarbonate.

Examples of protective groups for a carbonyl group of aldehydes include acetal-type protective groups such as dimethylacetal; and cyclic acetal-type protective groups such as cyclic 1,3-dioxane.

Examples of protective groups for a carbonyl group of ketones include ketal-type protective groups such as dimethyl ketal; cyclic ketal-type protective groups such as cyclic 1,3-dioxane; oxime-type protective groups such as O-methyloxime; and hydrazone-type protective groups such as N,N-dimethylhydrazone.

Examples of protective groups for a carboxy group include ester-type protective groups such as methyl ester; and amide-type protective groups such as N,N-dimethylamide.

Examples of protective groups for thiol include ether-type protective groups such as benzyl thioether; and ester-type protective groups such as thioacetate, thiocarbonate, and thiocarbamate.

Examples of protective groups for an amino group and aromatic heterocycles such as imidazole, pyrrole, and indole include carbamate-type protective groups such as benzylcarbamate; amide-type protective groups such as acetamide; alkylamine-type protective groups such as N-triphenylmethylamine; and sulfonamide-type protective groups such as methanesulfonamide.

Removal of a protective group may be performed by using a known method such as a method using an acid, a base, ultraviolet light, hydrazine, phenylhydrazine, sodium N-methyldithiocarbamate, tetrabutylammonium fluoride, palladium acetate, or trialkylsilyl halide (e.g., trimethylsilyl iodide, trimethylsilyl bromide), or by using a reduction method.

Examples of reductants to be used when reduction reaction is performed in each step include metal hydrides such as lithium aluminium hydride, sodium triacetoxyborohydride, sodium cyanoborohydride, diisobutylaluminium hydride (DIBAL-H), sodium borohydride, and tetramethylammonium triacetoxyborohydride; boranes such as a borane-tetrahydrofuran complex; Raney nickel; Raney cobalt; hydrogen; and formic acid. For example, Raney nickel or Raney cobalt may be used in the presence of hydrogen or formic acid. When a carbon-carbon double bond or triple bond is reduced, a method using a catalyst such as palladium-carbon and Lindlar's catalyst may be used.

Examples of oxidants to be used when oxidation reaction is performed in each step include peracids such as m-chloroperbenzoic acid (MCPBA), hydrogen peroxide, and t-butylhydroperoxide; perchlorates such as tetrabutylammonium perchlorate; chlorates such as sodium chlorate; chlorites such as sodium chlorite; periodates such as sodium periodate; hypervalent iodine reagents such as iodosylbenzene; manganese-containing reagents such as manganese dioxide and potassium permanganate; leads such as lead tetraacetate; chromium-containing reagents such as pyridinium chlorochromate (PCC), pyridinium dichromate (PDC), and the Jones reagent; halogen compounds such as N-bromosuccinimide (NBS); oxygen; ozone; a sulfur trioxide-pyridine complex; osmium tetroxide; selenium dioxide; and 2,3-dichloro-5,6-dicyano-1,4-benzoquinone (DDQ).

Examples of radical initiators to be used when radical cyclization reaction is performed in each step include azo compounds such as azobisisobutyronitrile (AIBN); water-soluble radical initiators such as 4-4'-azobis-4-cyanopentanoic acid (ACPA); triethylboron in the presence of air or oxygen; and benzoyl peroxide. Examples of radical reaction reagents to be used include tributylstannane, tristrimethylsilylsilane, 1,1,2,2-tetraphenyldisilane, diphenylsilane, and samarium iodide.

Examples of Wittig reagents to be used when the Wittig reaction is performed in each step include alkylidenephosphoranes. Alkylidenephosphoranes may be prepared by using a known method such as reaction of a phosphonium salt and a strong base.

Examples of reagents to be used when the Horner-Emmons reaction is performed in each step include phosphonoacetates such as methyl dimethylphosphonoacetate and ethyl diethylphosphonoacetate; and bases such as alkali metal hydrides and organolithiums.

Examples of reagents to be used when the Friedel-Crafts reaction is performed in each step include a Lewis acid with an acid chloride or an alkylating agent (e.g., a halogenated alkyl, an alcohol, an olefin). Alternatively, an organic acid or an inorganic acid may be used instead of a Lewis acid, and an acid anhydride such as acetic anhydride may be used instead of an acid chloride.

When aromatic nucleophilic substitution reaction is performed in each step, a nucleophile (e.g., an amine, imidazole) and a base (e.g., a basic salt, an organic base) are used as reagents.

Examples of bases used to generate a carbanion when nucleophilic addition reaction with a carbanion, nucleophilic 1,4-addition reaction with a carbanion (Michael addition reaction), or nucleophilic substitution reaction with a carbanion is performed in each step include organolithiums, metal alkoxides, inorganic bases, and organic bases.

Examples of Grignard reagents to be used when the Grignard reaction is performed in each step include arylmagnesium halides such as phenylmagnesium bromide; and alkylmagnesium halides such as methylmagnesium bromide and isopropylmagnesium bromide. Grignard reagents may be prepared by using a known method such as reaction of a halogenated alkyl or halogenated aryl and metal magnesium in a solvent of an ether or tetrahydrofuran.

When the Knoevenagel condensation reaction is performed in each step, an active methylene compound sandwiched between two electron-withdrawing groups (e.g., malonic acid, diethyl malonate, malononitrile) and a base (e.g., an organic base, a metal alkoxide, an inorganic base) are used as reagents.

When the Vilsmeier-Haack reaction is performed in each step, phosphoryl chloride and an amide derivative (e.g., N,N-dimethylformamide) are used as reagents.

Examples of azidating agents to be used when azidation reaction is performed for an alcohol, an alkyl halide, or a sulfonate in each step include diphenylphosphorylazide (DPPA), trimethylsilylazide, and sodium azide. When an alcohol is azidated, for example, a method using diphenylphosphorylazide and 1,8-diazabicyclo[5,4,0]undec-7-ene (DBU) or a method using trimethylsilylazide and a Lewis acid may be used.

Examples of reductants to be used when reductive amination reaction is performed in each step include sodium triacetoxyborohydride, sodium cyanoborohydride, hydrogen, and formic acid. Examples of carbonyl compounds to be used when the substrate is an amine compound include aldehydes such as paraformaldehyde as well as acetaldehyde, and ketones such as cyclohexanone. Examples of amines to be used when the substrate is a carbonyl compound include ammonia; primary amines such as methyl amine; and secondary amines such as dimethylamine.

When the Mitsunobu reaction is performed in each step, an azodicarboxylate (e.g., diethyl azodicarboxylate (DEAD), diisopropyl azodicarboxylate (DIAD)) and triphenylphosphine are used as reagents.

Examples of reagents to be used when esterification reaction, amidation reaction, or urea formation reaction is performed in each step include halogenated acyl forms such as acid chlorides and acid bromides; and activated carboxylic acids such as acid anhydrides, activated ester forms, and sulfate forms. Examples of activators for carboxylic acids include carbodiimide condensing agents such as 1-ethyl-3-(3-dimethylaminopropyl)carbodiimide hydrochloride (WSCD); triazine-based condensing agents such as 4-(4,6-dimethoxy-1,3,5-triazin-2-yl)-4-methylmorpholinium chloride-n-hydrate (DMT-MM); carbonate condensing agents such as 1,1-carbonyldiimidazole (CDI); diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate; O-(7-azabenzotriazol-1-yl)-N,N,N',N'-tetramethyluronium hexafluorophosphate (HATU); sulfuric acid; and any combination of them. When a carbodiimide condensing agent is used, an additive such as 1-hydroxybenzotriazol (HOBt), N-hydroxysuccinimide (HOSu), and dimethylaminopyridine (DMAP) may be further added to the reaction.

Examples of metal catalysts to be used when coupling reaction is performed in each step include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocenepalladium(II) chloride, and palladium(II) acetate; nickel compounds such as tetrakis(triphenylphosphine)nickel(0); rhodium compounds such as tris(triphenylphosphine)rhodium(III) chloride; cobalt compounds; copper compounds such as copper oxide and copper(I) iodide; and platinum compounds. A base may be further added to the reaction, and examples of the base include inorganic bases and basic salts.

When thiocarbonylation reaction is performed in each step, diphosphorus pentasulfide is typically used as a thiocarbonylating agent; however, not only diphosphorus pentasulfide, but also a reagent having 1,3,2,4-dithiadiphosphetane-2,4-disulfide structure such as 2,4-bis(4-methoxyphenyl)-1,3,2,4-dithiadiphosphetane-2,4-disulfide (Lowesson reagent) may be used.

Examples of halogenating agents to be used when the Wohl-Ziegler reaction is performed in each step include N-iodosuccinimide, N-bromosuccinimide (NBS), N-chlorosuccinimide (NCS), bromine, and sulfuryl chloride. Further, the reaction may be accelerated by addition of heat, light, or a radical initiator such as benzoyl peroxide and azobisisobutyronitrile.

Examples of halogenating agents to be used when halogenation reaction is performed for a hydroxy group in each step include hydrohalic acids and acid halides of inorganic acids, specifically, hydrochloric acid, thionyl chloride, phosphorus oxychloride for chlorination, and 48% hydrobromic acid for bromination. A method may be used in which a halogenated alkyl form is obtained from an alcohol by the action of triphenylphosphine and carbon tetrachloride, carbon tetrabromide, or the like. Alternatively, a method may be used in which a halogenated alkyl form is synthesized through two-step reaction such that an alcohol is converted into a sulfate and then reacted with lithium bromide, lithium chloride, or sodium iodide.

Examples of reagents to be used when the Arbuzov reaction is performed in each step include halogenated alkyls such as bromoethyl acetate; and phosphites such as triethylphosphite and tri(isopropyl)phosphite.

Examples of sulfonating agents to be used when sulfonation reaction is performed in each step include methanesulfonyl chloride, p-toluenesulfonyl chloride, methanesulfonic anhydride, p-toluenesulfonic anhydride, and trifluoromethanesulfonic anhydride.

When hydrolysis reaction is performed in each step, an acid or a base is used as a reagent. When acid hydrolysis reaction is performed for a t-butyl ester, formic acid or triethylsilane is added in some cases to reductively trap t-butyl cations produced as byproducts.

Examples of dehydrating agents to be used when dehydration reaction is performed in each step include sulfuric acid, diphosphorus pentoxide, phosphorus oxychloride, N,N'-dicyclohexylcarbodiimide, alumina, and polyphosphoric acid.

Compound (I) may be produced, for example, by using a production method shown below. Among the compounds (I), a compound in which each of the wavy lines forms a cis-structure and a compound in which one or both of the wave lines forms a trans-structure can be both produced by using the same production method as the production method shown below. In the present invention, compound (I) with a desired structure can be synthesized by using an appropriate raw material for the intended structure of compound (I) particularly in esterification. A salt of compound (I) can be obtained through appropriate mixing with an inorganic base, an organic base, an organic acid, or a basic or acidic amino acid.

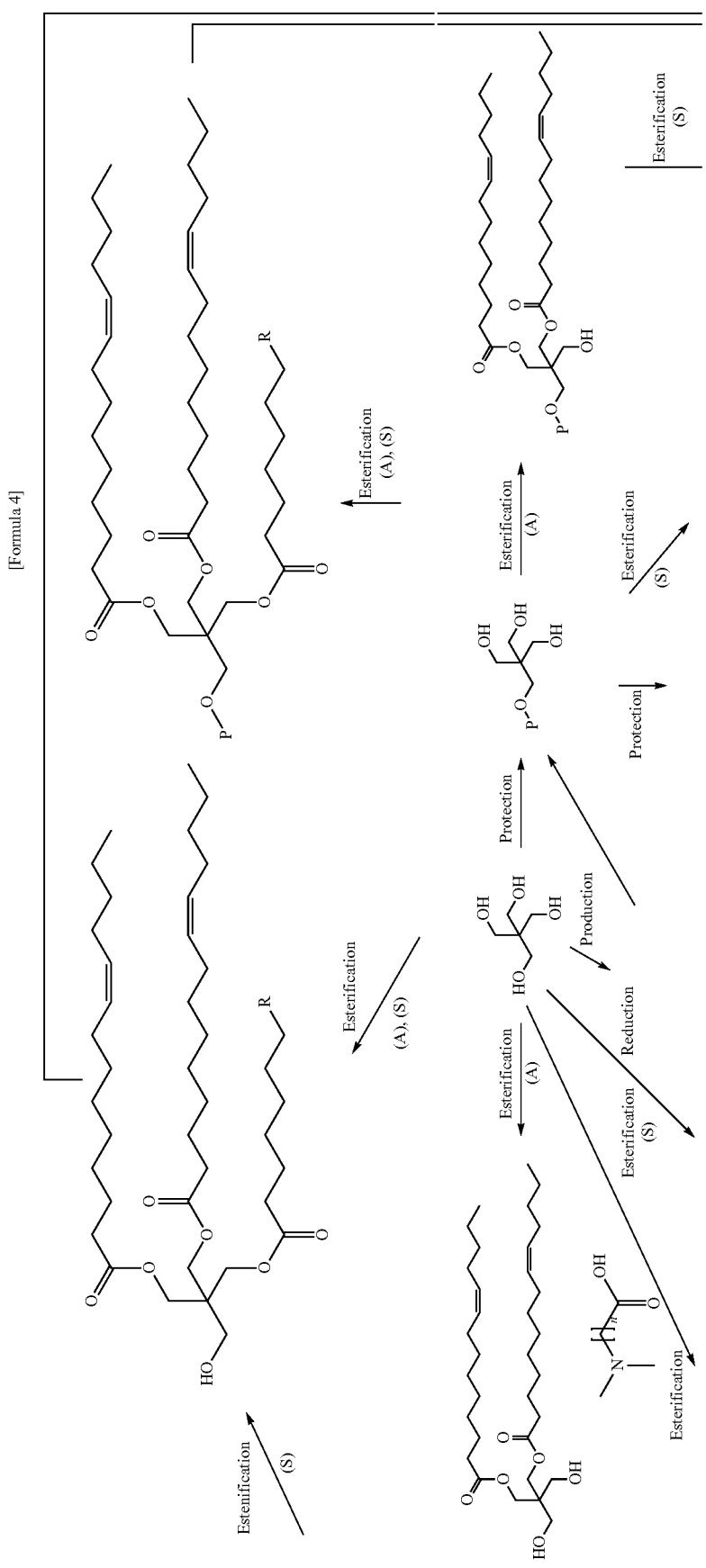
[Formula 4]

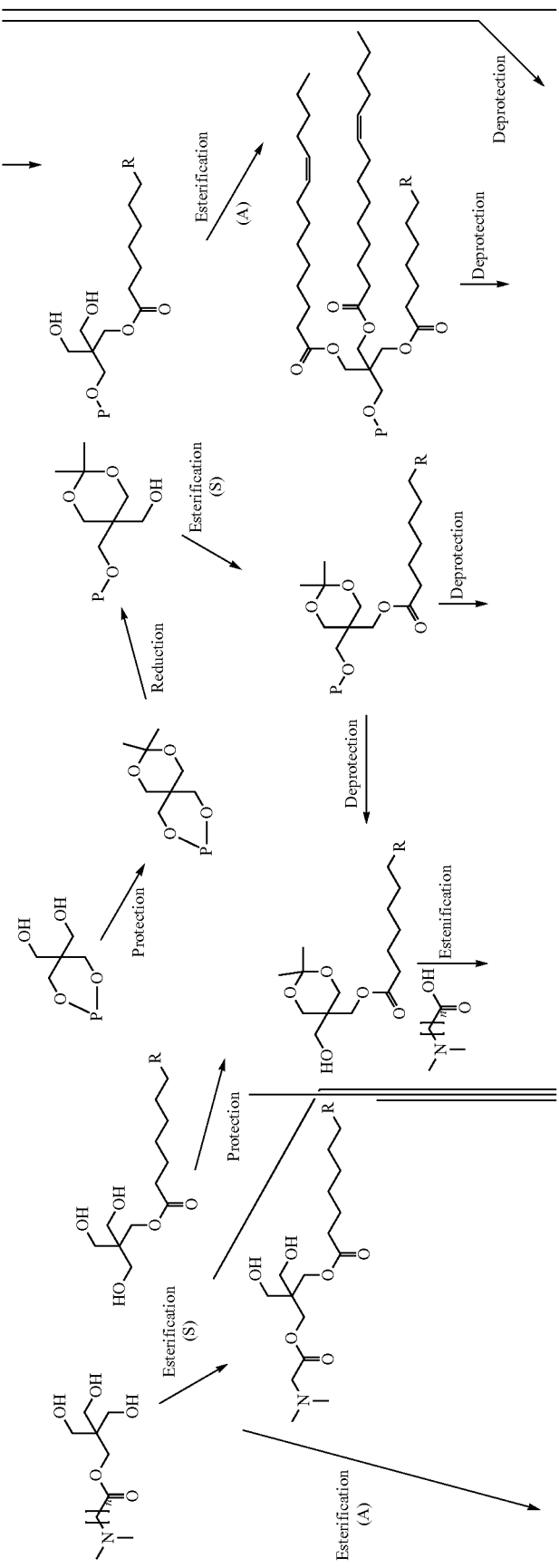

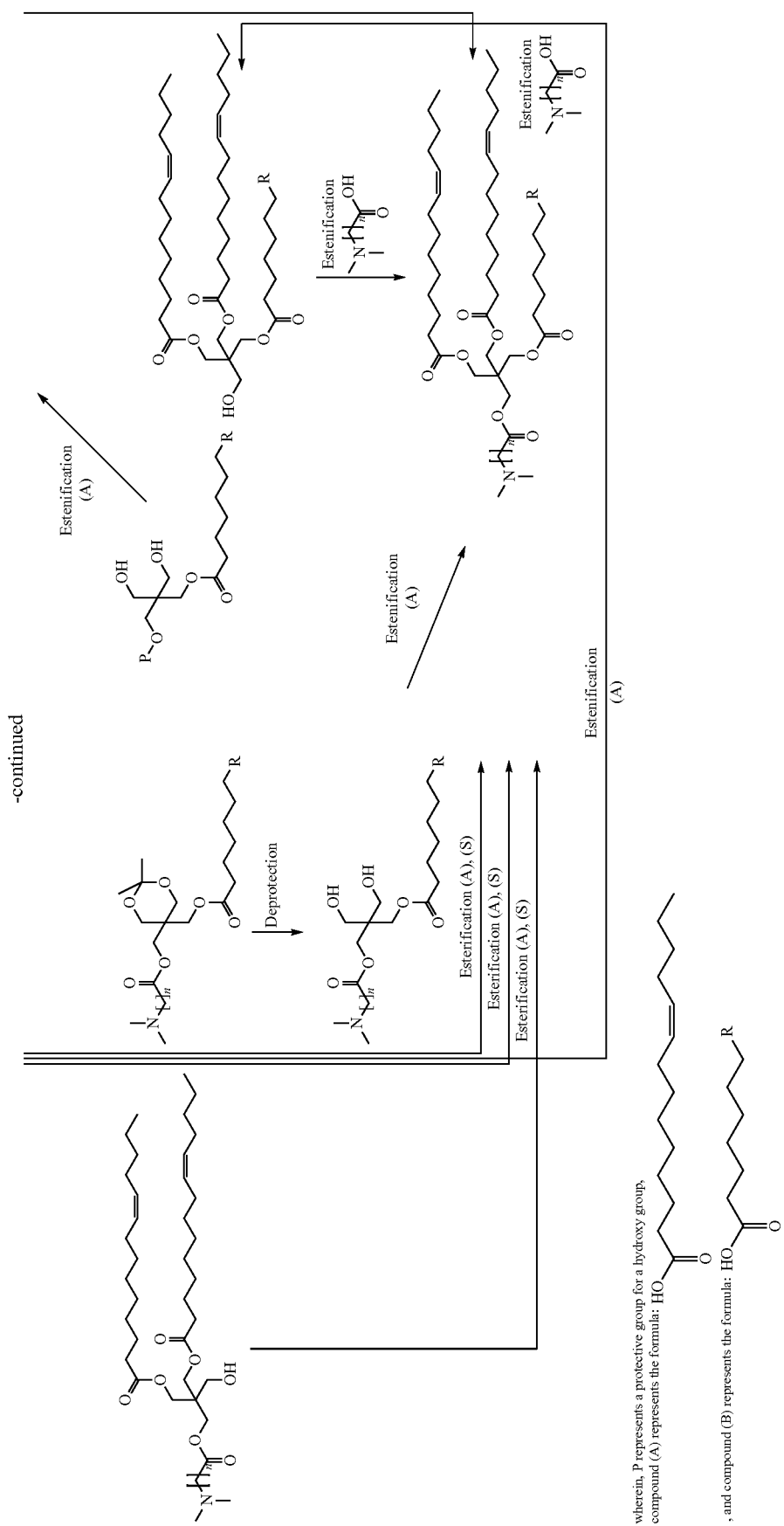
wherein, P represents a protective group for a hydroxy group, compound (A) represents the formula: 
, and compound (B) represents the formula:

Now, a method for producing a lipid particle containing the compound of the present invention and that for producing a composition containing the lipid particle and a nucleic acid for nucleic acid introduction will be described.

The lipid particle of the present invention can be produced by mixing the compound of the present invention (cationic lipid) and, as necessary, an additional lipid component, and then applying a known method to prepare a lipid particle from a lipid component. For example, the lipid particle can be produced as a lipid particle dispersion by dissolving the (mixed) lipid component in an organic solvent and mixing the resulting organic solvent solution with water or a buffer (e.g., through an emulsifying method). The mixing may be performed by using a microfluid mixing system (e.g., the apparatus NanoAssemblr (Precision NanoSystems)). The lipid particle obtained may be subjected to desalting or dialysis and sterile filtration. As necessary, pH adjustment or osmotic pressure adjustment may be performed.

Compound (I) can form different structures depending on combination of the definitions of n, R, and the wavy lines of formula (I). To produce the lipid particle, one compound having a specific structure may be used alone as compound (I), and a mixture of a plurality of compounds of different structures may be used as compound (I).

Examples of the "additional lipid component" include the above-mentioned structural lipids such as sterols, phospholipids, and polyethylene glycol lipids. The "additional lipid component" is used, for example, in an amount of 0.008 to 4 mol per mole of the compound of the present invention. The compound of the present invention is preferably used as a mixture with the additional lipid component (in particular, cholesterol, phosphatidylcholine, and a polyethylene glycol lipid). In a preferred embodiment using a mixture of the compound of the present invention and the additional lipid component, the mixture is a mixture of 1 to 4 mol of the compound of the present invention, 0 to 3 mol of a sterol, 0 to 2 mol of a phospholipid, and 0 to 1 mol of a polyethylene glycol lipid. In a more preferred embodiment using a mixture of the compound of the present invention and the additional lipid component, the mixture is a mixture of 1 to 1.5 mol of the compound of the present invention, 0 to 1.25 mol of a sterol, 0 to 0.5 mol of a phospholipid, and 0 to 0.125 mol of a polyethylene glycol lipid.

The concentration of the compound of the present invention or the mixture of the compound of the present invention and the additional lipid component in the organic solvent solution is preferably 0.5 to 100 mg/mL.

Examples of the organic solvent include methanol, ethanol, 1-propanol, 2-propanol, 1-butanol, tert-butanol, acetone, acetonitrile, N,N-dimethylformamide, dimethylsulfoxide, and mixtures of them. The organic solvent may contain 0 to 20% of water or a buffer.

Examples of the buffer include acidic buffers (e.g., acetate buffer, citrate buffer, 2-morpholinoethanesulfonate (MES) buffer, phosphate buffer), and neutral buffers (e.g., 4-(2-hydroxyethyl)-1-piperazineethanesulfonate (HEPES) buffer, tris(hydroxymethyl)aminomethane (Tris) buffer, phosphate buffer, phosphate-buffered saline (PBS)).

If mixing is performed by using a microfluid mixing system, it is preferred to mix 1 to 5 parts by volume of water or the buffer per part by volume of the organic solvent solution. The flow rate of the mixed solution (mixed solution of the organic solvent solution and water or the buffer) in the system is preferably 0.1 to 10 mL/min, and the temperature is preferably 15 to 45° C.

The composition of the present invention can be produced as a lipid particle dispersion containing an active ingredient by adding in advance a nucleic acid as an active ingredient to water or the buffer in production of the lipid particle or a lipid particle dispersion. The active ingredient is preferably added so that the active ingredient concentration of water or the buffer reaches 0.05 to 2.0 mg/mL.

In addition, the composition of the present invention can be produced as a lipid particle dispersion containing an active ingredient by admixing the lipid particle or a lipid particle dispersion and an active ingredient or an aqueous solution of the active ingredient through a known method. The lipid particle dispersion can be prepared by dispersing the lipid particle in an appropriate dispersion medium. The aqueous solution of the active ingredient can be prepared by dissolving the active ingredient in an appropriate solvent.

The content of the compound of the present invention in the composition of the present invention with the dispersion medium and solvent excluded is preferably 40 to 70% by weight.

The content of the active ingredient in the composition of the present invention with the dispersion medium and solvent excluded is preferably 1 to 20% by weight.

The dispersion medium of the lipid particle dispersion or the dispersion medium in the composition containing the composition can be replaced with water or a buffer through dialysis. The dialysis is performed with an ultrafiltration membrane having a molecular weight cutoff of 10 to 20K at 4° C. to room temperature. The dialysis may be repeatedly performed. For replacement of the dispersion medium, tangential flow filtration (TFF) may be used. After replacement of the dispersion medium, pH adjustment or osmotic pressure adjustment may be performed, as necessary.

Now, methods for analyzing a lipid particle containing the compound of the present invention, and a composition containing the lipid particle and a nucleic acid as an active ingredient will be described.

The particle size of the lipid particle (in the composition) can be measured by using a known means. For example, a Zetasizer Nano ZS (Malvern Instruments Limited), a particle size analyzer based on an NIBS (non-invasive backscatter) technique, can be used to calculate the particle size as a z-average particle size through cumulant analysis of the autocorrelation function. The particle size (average particle size) of the lipid particle (in the composition) is preferably 10 to 200 nm.

The concentration and encapsulation ratio of a nucleic acid (e.g., an siRNA, an mRNA) as an active ingredient in the composition of the present invention can be measured by using a known means. For example, after the nucleic acid is fluorescence-labeled with Quant-iT™ RiboGreen® (Invitrogen), the concentration and the encapsulation ratio can be determined by measuring the fluorescence intensity. The concentration of the nucleic acid in the composition can be calculated by using a standard curve prepared from aqueous solutions of the nucleic acid with known concentrations, and the encapsulation ratio can be calculated on the basis of difference in fluorescence intensity depending on the presence or absence of addition of Triton-X100 (a surfactant to disintegrate the lipid particle). The concentration of the nucleic acid in the composition refers to the total concentration of molecules of the nucleic acid encapsulated in the lipid particle and molecules of the nucleic acid not encapsulated in the lipid particle, and the encapsulation ratio refers to the fraction of molecules of the nucleic acid encapsulated in the lipid particle to all the molecules of the nucleic acid in the composition.

EXAMPLES

The present invention will be further described in detail with reference to Examples, Test Examples, and Formulation Examples; however, these do not limit the present invention, and modification may be made without departing from the scope of the present invention.

"Room temperature" in Examples below typically indicates approximately 10° C. to approximately 35° C. Each ratio shown for mixed solvent indicates a volume ratio, unless otherwise stated. % indicates % by weight, unless otherwise stated.

Elution in column chromatography was performed under observation with TLC (thin-layer chromatography), unless otherwise described. In TLC observation, a 60 $F_2 54$ produced by Merck KGaA was used as a TLC plate, and a solvent used as an elution solvent in column chromatography was used as an eluent. A UV detector was employed for detection, and observation was performed with a TLC coloring reagent, as necessary. In description of silica gel column chromatography, NH indicates that aminopropylsilane-bonded silica gel was used, and Diol indicates that 3-(2,3-dihydroxypropoxy)propylsilane-bonded silica gel was used. In description of preparative HPLC (high-performance liquid chromatography), C18 indicates that octadecyl-bonded silica gel was used. Each ratio shown for elution solvent indicates a volume ratio, unless otherwise stated.

$^1$H NMR was measured by using a Fourie transformation-NMR. The software ACD/SpecManager (product name) and so on were used for $^1$H NMR analysis. Description is occasionally omitted for peaks for a hydroxy group, an amino group, and so on with a very broad proton peak.

MS was measured through an LC/MS and an MALDI/TOFMS. For the ionization method, an ESI method, an APCI method, or an MALDI method was used. CHCA was used for the matrix. Measured values (found) were reported as data. In typical cases, some molecular ion peaks are observed as fragment ions. In the case of a salt, a molecular ion peak for the free form, or cationic, anionic, or fragment ion peaks are typically observed.

In Examples below, the following abbreviations are used.
MS: Mass spectrum
M: Molar concentration
N: Normality
$CDCl_3$: Deuterated chloroform
DMSO-$d_6$: Deuterated dimethylsulfoxide
$^1$H NMR: Proton nuclear magnetic resonance
LC/MS: Liquid chromatograph/mass spectrometer
ESI: Electrospray ionization
APCI: Atmospheric pressure chemical ionization
MALDI: Matrix-assisted laser desorption/ionization
TOFMS: Time-of-flight mass spectrometry
CHCA: a-Cyano-4-hydroxycinnamic acid
DMF: N,N-dimethylformamide
THF: Tetrahydrofuran
DMAP: 4-Dimethylaminopyridine
TBAF: Tetrabutylammonium fluoride

[Example 1] 3-((4-(Dimethylamino)butanoyl)oxy)-2,2-bis(((9Z)-tetradec-9-enoyloxy)methyl)propyl (9Z)-tetradec-9-enoate A) 2-(((tert-Butyldimethylsilyl)oxy)methyl)-2-(hydroxymethyl)propane-1,3-diol To a mixture of 2,2-bis(hydroxymethyl)propane-1,3-diol (5.45 g), 1H-imidazole (2.72 g) and DMF (190 mL), a solution of tert-butylchlorodimethylsilane (3.01 g) in DMF (10 mL) was added at room temperature. After stirring for 24 hours, the reaction mixture was concentrated under reduced pressure. The residue was diluted with ethyl acetate, washed three times with water and once with saturated brine, and then dried over anhydrous sodium sulfate, and the solvent was distilled off under reduced pressure. The residue was purified by silica gel column chromatography (ethyl acetate/hexane) to afford the title compound (2.25 g).

$^1$H NMR (300 MHz, $CDCl_3$) δ ppm 0.08 (6H, s), 0.90 (9H, s), 2.53 (3H, t, J=5.5 Hz), 3.66 (2H, s), 3.73 (6H, d, J=5.5 Hz)

B) 3-((tert-Butyl(dimethyl)silyl)oxy)-2,2-bis(((9Z)-tetradec-9-enoyloxy)methyl)propyl (9Z)-tetradec-9-enoate To a solution of 2-(((tert-butyldimethylsilyl)oxy)methyl)-2-(hydroxymethyl)propane-1,3-diol (258 mg), (9Z)-tetradec-9-enoic acid (769 mg) and DMAP (126 mg) in DMF (3 mL), 1-ethyl-3-(3-dimethylaminopropyl)carbodiimide hydrochloride (790 mg) was added at room temperature. After stirring for 18 hours, the reaction mixture was diluted with ethyl acetate, washed twice with water and once with saturated brine, and then dried over anhydrous sodium sulfate, and the solvent was distilled off under reduced pressure. The residue was purified by silica gel column chromatography (NH, ethyl acetate/hexane) to afford the title compound (860 mg).

$^1$H NMR (300 MHz, $CDCl_3$) δ ppm 0.03 (6H, s), 0.81-0.96 (18H, m), 1.18-1.41 (36H, m), 1.53-1.67 (6H, m), 1.91-2.10 (12H, m), 2.29 (6H, t, J=7.6 Hz), 3.58 (2H, s), 4.08 (6H, s), 5.27-5.43 (6H, m)

C) 3-Hydroxy-2,2-bis(((9Z)-tetradec-9-enoyloxy)methyl)propyl (9Z)-tetradec-9-enoate To a solution of 3-((tert-butyl(dimethyl)silyl)oxy)-2,2-bis(((9Z)-tetradec-9-enoyloxy)methyl)propyl (9Z)-tetradec-9-enoate (5.91 g) in THF (120 mL), a mixture of a THF solution of TBAF (1 M, 14.85 mL) and acetic acid (4.91 mL) was added at room temperature. After stirring for 3 days, the reaction mixture was concentrated under reduced pressure. The residue was diluted with ethyl acetate, washed once with saturated aqueous solution of sodium hydrogen carbonate and once with saturated brine, and then dried over anhydrous sodium sulfate, and the solvent was distilled off under reduced pressure. The residue was purified by silica gel column chromatography (ethyl acetate/hexane) to afford the title compound (4.96 g).

$^1$H NMR (300 MHz, $CDCl_3$) δ ppm 0.82-0.97 (9H, m), 1.16-1.42 (36H, m), 1.52-1.68 (6H, m), 1.90-2.12 (12H, m), 2.32 (6H, t, J=7.6 Hz), 2.52 (1H, t, J=7.0 Hz), 3.49 (2H, d, J=7.0 Hz), 4.11 (6H, s), 5.26-5.42 (6H, m)

D) 3-((4-(Dimethylamino)butanoyl)oxy)-2,2-bis(((9Z)-tetradec-9-enoyloxy)methyl)propyl (9Z)-tetradec-9-enoate To a solution of 3-hydroxy-2,2-bis(((9Z)-tetradec-9-enoyloxy)methyl)propyl (9Z)-tetradec-9-enoate (4.96 g), DMAP (796 mg) and 4-(dimethylamino)butanoic acid hydrochloride (2.19 g) in DMF (20 mL), 1-ethyl-3-(3-dimethylaminopropyl)carbodiimide hydrochloride (2.50 g) was added at room temperature. After stirring for 18 hours, the reaction mixture was diluted with ethyl acetate, washed once with saturated aqueous solution of sodium hydrogen carbonate and once with saturated brine, and then dried over anhydrous sodium sulfate, and the solvent was distilled off under reduced pressure. The residue was purified by silica gel column chromatography (NH, ethyl acetate/hexane) to afford the title compound (5.31 g).

$^1$H NMR (300 MHz, CDCl$_3$) δ ppm 0.82-0.94 (9H, m), 1.20-1.42 (36H, m), 1.50-1.66 (6H, m), 1.69-1.83 (2H, m), 1.90-2.10 (12H, m), 2.20 (6H, s), 2.23-2.41 (10H, m), 4.11 (8H, s), 5.23-5.44 (6H, m)

[Example 4] 3-((4-(Dimethylamino)butanoyl)oxy)-2,2-bis(((9Z)-tetradec-9-enoyloxy)methyl)propyl (9Z)-hexadec-9-enoate A) 2-(((tert-Butyl(diphenyl)silyl)oxy)methyl)-2-(hydroxymethyl)propane-1,3-diol To a mixture of 2,2-bis(hydroxymethyl)propane-1,3-diol (5.0 g), 1H-imidazole (2.5 g) and DMF (200 mL), a solution of tert-butylchlorodiphenylsilane (5.1 g) in DMF (10 mL) was added at room temperature. After stirring for 18 hours, the reaction mixture was concentrated under reduced pressure. The residue was diluted with ethyl acetate, washed three times with water and once with saturated brine, and dried over anhydrous sodium sulfate, and the solvent was distilled off under reduced pressure. The residue was purified by silica gel column chromatography (ethyl acetate/hexane) to afford the title compound (6.4 g).

$^1$H NMR (500 MHz, CDCl$_3$) δ ppm 1.07 (9H, s), 2.34 (3H, t, J=5.5 Hz), 3.67 (2H, s), 3.74 (6H, d, J=5.5 Hz), 7.39-7.48 (6H, m), 7.63-7.67 (4H, m)

B) (5-(((tert-Butyl(diphenyl)silyl)oxy)methyl)-2,2-dimethyl-1,3-dioxan-5-yl)methanol To a solution of 2-(((tert-butyl(diphenyl)silyl)oxy)methyl)-2-(hydroxymethyl)propane-1,3-diol (3.5 g) and 2,2-dimethoxypropane (1.5 g) in acetone (35 mL), p-toluenesulfonic acid monohydrate (88.9 mg) was added at room temperature. After stirring for 2 hours, diluted aqueous ammonia was added to the reaction mixture to neutralize the reaction mixture, and the solvent was then distilled off under reduced pressure. The residue was purified by silica gel column chromatography (ethyl acetate/hexane) to afford the title compound (2.7 g).

$^1$H NMR (500 MHz, CDCl$_3$) δ ppm 1.07 (9H, s), 1.27 (3H, s), 1.41 (3H, s), 2.12-2.18 (1H, m), 3.69-3.78 (8H, m), 7.38-7.47 (6H, m), 7.65-7.69 (4H, m)

C) (5-(((tert-Butyl(diphenyl)silyl)oxy)methyl)-2,2-dimethyl-1,3-dioxan-5-yl)methyl (9Z)-hexadec-9-enoate To a solution of (5-(((tert-butyl(diphenyl)silyl)oxy)methyl)-2,2-dimethyl-1,3-dioxan-5-yl)methanol (910 mg), DMAP (215 mg) and (9Z)-hexadec-9-enoic acid (838 mg) in DMF (10 mL), 1-ethyl-3-(3-dimethylaminopropyl)carbodiimide hydrochloride (757 mg) was added at room temperature. After stirring for 6 hours, ethyl acetate was added to the reaction mixture, the resultant was washed twice with water and once with saturated brine, and then dried over anhydrous sodium sulfate, and the solvent was distilled off under reduced pressure. The residue was purified by silica gel column chromatography (ethyl acetate/hexane) to afford the title compound (1.43 g).

$^1$H NMR (500 MHz, CDCl$_3$) δ ppm 0.84-0.91 (3H, m), 1.03-1.07 (9H, m), 1.22-1.35 (16H, m), 1.40 (6H, d, J=17.0 Hz), 1.49-1.63 (2H, m), 2.01 (4H, q, J=6.5 Hz), 2.24 (2H, t, J=7.6 Hz), 3.65 (2H, s), 3.73 (2H, d, J=11.7 Hz), 3.80 (2H, d, J=12.0 Hz), 4.17 (2H, s), 5.29-5.39 (2H, m), 7.35-7.46 (6H, m), 7.65 (4H, d, J=6.9 Hz)

D) (5-(Hydroxymethyl)-2,2-dimethyl-1,3-dioxan-5-yl)methyl (9Z)-hexadec-9-enoate

To a solution of (5-(((tert-butyl(diphenyl)silyl)oxy)methyl)-2,2-dimethyl-1,3-dioxan-5-yl)methyl (9Z)-hexadec-9-enoate (1.43 g) in THF (4 mL), a THF solution of TBAF (1 M, 2.64 mL) was added at room temperature. After stirring for 3 hours, the reaction mixture was concentrated under reduced pressure. The residue was diluted with ethyl acetate, washed once with saturated aqueous solution of sodium hydrogen carbonate and once with saturated brine, and then dried over anhydrous sodium sulfate, and the solvent was distilled off under reduced pressure. The residue was purified by silica gel column chromatography (ethyl acetate/hexane) to afford the title compound (0.82 g).

$^1$H NMR (500 MHz, CDCl$_3$) δ ppm 0.85-0.91 (3H, m), 1.24-1.36 (16H, m), 1.42 (6H, s), 1.58-1.66 (2H, m), 2.01 (4H, q, J=6.5 Hz), 2.30 (1H, t, J=6.6 Hz), 2.35 (2H, t, J=7.6 Hz), 3.48 (2H, d, J=6.6 Hz), 3.69-3.75 (4H, m), 4.25 (2H, s), 5.31-5.38 (2H, m)

E) (5-(((4-(Dimethylamino)butanoyl)oxy)methyl)-2,2-dimethyl-1,3-dioxan-5-yl)methyl (9Z)-hexadec-9-enoate To a solution of (5-(hydroxymethyl)-2,2-dimethyl-1,3-dioxan-5-yl)methyl (9Z)-hexadec-9-enoate (410 mg), DMAP (97 mg) and 4-(dimethylamino)butyric acid hydrochloride (250 mg) in DMF (4 mL), 1-ethyl-3-(3-dimethylaminopropyl)carbodiimide hydrochloride (343 mg) was added at 50° C. After stirring for 4 hours, ethyl acetate was added to the reaction mixture, the resultant was washed twice with water and once with saturated brine, and then dried over anhydrous sodium sulfate, and the solvent was then distilled off under reduced pressure. The residue was purified by silica gel column chromatography (NH, ethyl acetate/hexane) to afford the title compound (430 mg).

$^1$H NMR (500 MHz, CDCl$_3$) δ ppm 0.86-0.91 (3H, m), 1.24-1.36 (16H, m), 1.42 (6H, s), 1.53-1.69 (2H, m), 1.78 (2H, m), 1.98-2.04 (4H, m), 2.21 (6H, s), 2.29 (4H, m), 2.37 (2H, t, J=7.6 Hz), 3.74 (4H, s), 4.11 (4H, d, J=5.7 Hz), 5.31-5.38 (2H, m)

F) 3-((4-(Dimethylamino)butanoyl)oxy)-2,2-bis(((9Z)-tetradec-9-enoyloxy)methyl)propyl (9Z)-hexadec-9-enoate To (5-(((4-(dimethylamino)butanoyl)oxy)methyl)-2,2-dimethyl-1,3-dioxan-5-yl)methyl (9Z)-hexadec-9-enoate (430 mg), acetic acid (2 mL) and water (1 mL) were added, and the resultant was stirred at 75° C. for 2 hours, and the solvent was then distilled off under reduced pressure. Ethyl acetate and saturated aqueous solution of sodium hydrogen carbonate were added to the residue, and the resultant was stirred for 2 hours. After washing with water was performed twice, the resultant was dried over anhydrous sodium sulfate, and the solvent was 1a then distilled off under reduced pressure. To a solution of the resulting residue, DMAP (201 mg) and (9Z)-tetradec-9-enoic acid (466 mg) in DMF (4 mL), 1-ethyl-3-(3-dimethylaminopropyl)carbodiimide hydrochloride (458 mg) was added at 50° C. After stirring for 4 hours, ethyl acetate was added to the reaction mixture, the resultant was washed twice with water and once with saturated brine, and then dried over anhydrous sodium sulfate, and the solvent was then distilled off under reduced pressure. The residue was purified by silica gel column chromatography (NH, ethyl acetate/hexane) to afford the title compound (604 mg).

$^1$H NMR (500 MHz, CDCl$_3$) δ ppm 0.85-0.92 (9H, m), 1.24-1.36 (40H, m), 1.55-1.64 (6H, m), 1.73-1.80 (2H, m), 1.98-2.05 (12H, m), 2.20 (6H, s), 2.24-2.33 (8H, m), 2.36 (2H, t, J=7.6 Hz), 4.09-4.13 (8H, m), 5.31-5.38 (6H, m)

[Example 8] 2-(((N,N-Dimethyl-p-alanyl)oxy)methyl)-2-((octanoyloxy)methyl)propane-1,3-diyl (9Z,9'Z)bis-tetradec-9-enoate A) (2-(4-Methoxyphenyl)-1,3-dioxane-5,5-diyl)dimethanol A solution of 2,2-bis(hydroxymethyl)propane-1,3-diol (506 g) in water (2.0 L) was stirred at 50° C. Concentrated hydrochloric acid (18 mL) was added thereto, to which p-methoxybenzaldehyde (474 mL) was added dropwise at around 30° C. over 3 hours. Thereafter, the temperature of the reaction solution was adjusted to 25° C., and the reaction solution was stirred for 5 hours. Thereto, 2 N aqueous solution of sodium hydroxide (120 mL) was added, and the resultant was stirred for 1 hour. Crystals were collected through filtration and washed with water, and then recrystallization was performed with ethyl acetate/hexane to afford the title compound (769 g).

$^1$H NMR (500 MHz, DMSO-d$_6$) δ ppm 3.24 (2H, d, J=5.0 Hz), 3.67 (2H, d, J=5.4 Hz), 3.74 (3H, s), 3.77 (2H, d, J=11.3 Hz), 3.88 (2H, t, J=11.3 Hz), 4.53 (1H, t, J=5.4 Hz), 4.62 (1H, t, J=5.0 Hz), 5.34 (1H, s), 6.90 (2H, d, J=8.9 Hz), 7.33 (2H, d, J=8.9 Hz)

B-1) 2-(Hydroxymethyl)-2-(((4-methoxybenzyl)oxy)methyl)propane-1,3-diol

To a suspension solution of (2-(4-methoxyphenyl)-1,3-dioxane-5,5-diyl)dimethanol (10.0 g) in toluene (100 mL), 1.5 M DIBAL-H solution (105 mL) was added dropwise at room temperature, and the resultant was stirred for 5 hours. Methanol (30 mL) was added thereto, and 2 N hydrochloric acid (20 mL) and 4 N aqueous solution of sodium hydroxide (240 mL) were then added thereto and the resultant was stirred for 2 hours, and thereafter the toluene layer was removed. After the aqueous layer was neutralized with hydrochloric acid, extraction was performed with ethyl acetate, and the extract was washed twice with saturated brine and filtered through a Celite. The solvent was distilled off under reduced pressure, and the residue was recrystallized with ethyl acetate/hexane to afford the title compound (6.6 g).

$^1$H NMR (500 MHz, DMSO-d$_6$) δ ppm 3.32 (2H, s), 3.39 (6H, d, J=5.4 Hz), 3.74 (3H, s), 4.21 (3H, t, J=5.4 Hz), 4.36 (2H, s), 6.90 (2H, d like, J=7.8 Hz), 7.23 (2H, d like, J=7.8 Hz)

C-1) (5-(((4-Methoxybenzyl)oxy)methyl)-2,2-dimethyl-1,3-dioxan-5-yl)methanol

To a solution of 2-(hydroxymethyl)-2-(((4-methoxybenzyl)oxy)methyl)propane-1,3-diol (1.00 g) and 2,2-dimethoxypropane (1.22 g) in DMF (5 mL), pyridinium p-toluenesulfonate (10 mg) was added at room temperature. After stirring for 2 hours, ethyl acetate was added to the reaction mixture, the resultant was washed once with saturated aqueous solution of sodium hydrogen carbonate and twice with 5% saline, and then dried over anhydrous sodium sulfate, and the solvent was distilled off under reduced pressure. The residue was purified by silica gel column chromatography (ethyl acetate/hexane) to afford the title compound (426 mg).

$^1$H NMR (500 MHz, DMSO-d$_6$) δ ppm 1.29 (3H, s), 1.29 (3H, s), 3.35 (2H, s), 3.39 (2H, d, J=5.1 Hz), 3.61 (4H, s), 3.74 (3H, s), 4.38 (2H, s), 4.59 (1H, t, J=5.1 Hz), 6.90 (2H, d like, J=7.5 Hz), 7.24 (2H, d like, J=7.5 Hz)

B-2) 9-(4-Methoxyphenyl)-3,3-dimethyl-2,4,8,10-tetraoxaspiro[5.5]undecane

To a solution of (2-(4-methoxyphenyl)-1,3-dioxane-5,5-diyl)dimethanol (2.00 g) and 2,2-dimethoxypropane (2.46 g) in DMF (8 mL), pyridinium p-toluenesulfonate (20 mg) was added at room temperature. After stirring for 4 hours, the reaction mixture was diluted with ethyl acetate, washed twice with saturated aqueous solution of sodium hydrogen carbonate and twice with saturated brine, and then dried over anhydrous magnesium sulfate, and the solvent was then distilled off under reduced pressure. The residue was recrystallized with ethyl acetate/hexane to afford the title compound (1.62 g).

$^1$H NMR (500 MHz, DMSO-d$_6$) δ ppm 1.34 (6H, s), 3.33 (2H, s), 3.63 (2H, d, J=11.7 Hz), 3.74 (3H, s), 3.99 (2H, s), 4.12 (2H, d, J=11.7 Hz), 5.37 (1H, s), 6.90 (2H, d, J=8.8 Hz), 7.34 (2H, d, J=8.81 Hz)

C-2) (5-(((4-Methoxybenzyl)oxy)methyl)-2,2-dimethyl-1,3-dioxan-5-yl)methanol

To a suspension solution of 9-(4-methoxyphenyl)-3,3-dimethyl-2,4,8,10-tetraoxaspiro(5.5]undecane (22.0 g) in toluene (200 mL), 1.5 M DIBAL-H solution (60 mL) was added dropwise at 5 to 20° C., and the resultant was stirred at 15° C. for 3 hours. Methanol (22 mL) was added thereto, and 2 N aqueous solution of sodium hydroxide (100 mL) and 4 N aqueous solution of sodium hydroxide (200 mL) were then added dropwise thereto in the order presented. After stirring for 1.5 hours, the toluene layer was separated and washed with 5% saline. The solvent was distilled off under reduced pressure. The residue was purified by silica gel column chromatography (ethyl acetate/hexane) to afford the title compound (14.7 g).

$^1$H NMR (500 MHz, DMSO-d6) δ ppm 1.29 (3H, s), 1.29 (3H, s), 3.35 (2H, s), 3.39 (2H, d, J=5.1 Hz), 3.61 (4H, s), 3.74 (3H, s), 4.38 (2H, s), 4.59 (1H, t, J=5.1 Hz), 6.90 (2H, d like, J=7.5 Hz), 7.24 (2H, d like, J=7.5 Hz)

D) (5-(((4-Methoxybenzyl)oxy)methyl)-2,2-dimethyl-1,3-dioxan-5-yl)methyl octanoate To a solution of (5-(((4-methoxybenzyl)oxy)methyl)-2,2-dimethyl-1,3-dioxan-5-yl)methanol (2.00 g), DMAP (412 mg) and octanoic acid (1.27 g) in DMF (20 mL), 1-ethyl-3-(3-dimethylaminopropyl)carbodiimide hydrochloride (1.94 g) was added at 50° C. After stirring for 4 hours, ethyl acetate was added to the reaction mixture, the resultant was washed twice with water and once with saturated brine, and then dried over anhydrous sodium sulfate, and the solvent was then distilled off under reduced pressure. The residue was purified by silica gel column chromatography (ethyl acetate/hexane) to afford the title compound (2.78 g).

$^1$H NMR (500 MHz, CDCl$_3$) δ 0.84-0.91 (3H, m), 1.22-1.33 (8H, m), 1.40 (6H, s), 1.53-1.61 (2H, m), 2.26 (2H, t, J=7.6 Hz), 3.39 (2H, s), 3.68-3.74 (2H, m), 3.76-3.80 (2H, m), 3.80 (3H, s), 4.15 (2H, s), 4.42 (2H, s), 6.87 (2H, d, J=7.8 Hz), 7.20-7.24 (2H, m)

E) (5-(Hydroxymethyl)-2,2-dimethyl-1,3-dioxan-5-yl)methyl octanoate

To a solution of (5-(((4-methoxybenzyl)oxy)methyl)-2,2-dimethyl-1,3-dioxan-5-yl)methyl octanoate (2.78 g) in ethanol (30 mL), Pd-carbon (840 mg) was added at room temperature, and the resultant was stirred under a hydrogen atmosphere for 5 hours. After the reaction, Pd-carbon was removed through filtration, and the solvent was then distilled off under reduced pressure. The residue was purified by silica gel column chromatography (ethyl acetate/hexane) to afford the title compound (1.35 g).
$^1$H NMR (500 MHz, CDCl$_3$) δ 0.85-0.91 (3H, m), 1.23-1.34 (8H, m), 1.38-1.44 (6H, m), 1.63 (2H, m), 2.30-2.38 (3H, m), 3.48 (2H, d, J=6.6 Hz), 3.68-3.75 (4H, m), 4.25 (2H, s)

F) (5-(((N,N-Dimethyl-p-alanyl)oxy)methyl)-2,2-dimethyl-1,3-dioxan-5-yl)methyl octanoate To a solution of (5-(hydroxymethyl)-2,2-dimethyl-1,3-dioxan-5-yl)methyl octanoate (400 mg), DMAP (129 mg) and 3-(dimethylamino)propanoic acid hydrochloride (305 mg) in DMF (4 mL), 1-ethyl-3-(3-dimethylaminopropyl)carbodiimide hydrochloride (456 mg) was added at room temperature. After stirring for 4 hours, ethyl acetate was added to the reaction mixture, the resultant was washed twice with water and once with saturated brine, and then dried over anhydrous sodium sulfate, and the solvent was then distilled off under reduced pressure. The residue was purified by silica gel column chromatography (NH, ethyl acetate/hexane) to afford the title compound (320 mg).
$^1$EH NMR (500 MHz, CDCl$_3$) δ 0.84-0.92 (3H, m), 1.21-1.33 (8H, m), 1.42 (6H, s), 1.61 (2H, br), 2.23 (6H, s), 2.32 (2H, t, J=7.6 Hz), 2.47-2.51 (2H, m), 2.57-2.61 (2H, m), 3.75 (4H, s), 4.13 (4H, d, J=11.7 Hz)

G) 2-(((N,N-Dimethyl-1-alanyl)oxy)methyl)-2-((octanoyloxy)methyl)propane-1,3-diyl (9Z,9'Z)bis-tetradec-9-enoate To (5-(((N,N-dimethyl-p-alanyl)oxy)methyl)-2,2-dimethyl-1,3-dioxan-5-yl)methyl octanoate (320 mg), acetic acid (1.6 mL) and water (0.8 mL) were added, and the resultant was stirred at 65° C. for 3.5 hours, and the solvent was then distilled off under reduced pressure. Ethyl acetate and saturated aqueous solution of sodium hydrogen carbonate were added to the residue, and the resultant was stirred for 2 hours. After washing was performed twice with water and once with saturated brine, the resultant was dried over anhydrous sodium sulfate, and the solvent was then distilled off under reduced pressure. To a solution of the resulting residue (150 mg), DMAP (101 mg), and (9Z)-tetradec-9-enoic acid (235 mg) in DMF (4.5 mL), 1-ethyl-3-(3-dimethylaminopropyl)carbodiimide hydrochloride (231 mg) was added at 50° C. After stirring for 8 hours, ethyl acetate was added to the reaction mixture, the resultant was washed twice with water and once with saturated brine, and then dried over anhydrous sodium sulfate, and the solvent was then distilled off under reduced pressure. The residue was purified by silica gel column chromatography (NH, ethyl acetate/hexane) to afford the title compound (230 mg).
$^1$H NMR (500 MHz, CDCl$_3$) δ 0.84-0.93 (9H, m), 1.24-1.36 (30H, m), 1.53-1.65 (8H, m), 1.98-2.05 (8H, m), 2.22 (6H, s), 2.30 (6H, t, J=7.6 Hz), 2.48 (2H, t, J=6.9 Hz), 2.58 (2H, t, J=6.8 Hz), 4.06-4.22 (8H, m), 5.31-5.38 (4H, m)

[Example 11] 2-(((4-(Dimethylamino)butanoyl)oxy)methyl)-2-((dodecanoyloxy)methyl)propane-1,3-diyl (9Z,9'Z)bis-tetradec-9-enoate

A) 3-Hydroxy-2,2-bis(hydroxymethyl)propyl Dodecanoate

To a solution of 2,2-bis(hydroxymethyl)propane-1,3-diol (5.00 g), DMAP (2.24 g) and lauric acid (3.68 g) in DMF (150 mL), 1-ethyl-3-(3-dimethylaminopropyl)carbodiimide hydrochloride (7.04 g) was added at room temperature. After stirring for 20 hours, ethyl acetate was added to the reaction mixture, the resultant was washed twice with water and once with saturated brine, and then dried over anhydrous sodium sulfate, and the solvent was then distilled off under reduced pressure. The residue was purified by silica gel column chromatography (ethyl acetate/hexane) to afford the title compound (1.79 g).
$^1$H NMR (500 MHz, CDCl$_3$) δ 0.85-0.91 (3H, m), 1.22-1.33 (16H, m), 1.59-1.66 (3H, m), 2.36 (2H, t, J=7.6 Hz), 2.51 (2H, t, J=5.8 Hz), 3.65 (6H, d, J=5.7 Hz), 4.23 (2H, s)

B) 2-((Dodecanoyloxy)methyl)-2-(hydroxymethyl)propane-1,3-diyl (9Z,9'Z)bis-tetradec-9-enoate To a solution of 3-hydroxy-2,2-bis(hydroxymethyl)propyl dodecanoate (400 mg), DMAP (153 mg) and (9Z)-tetradec-9-enoic acid (569 mg) in DMF (4 mL), 1-ethyl-3-(3-dimethylaminopropyl)carbodiimide hydrochloride (602 mg) was added at room temperature. After stirring for 8 hours, ethyl acetate was added to the reaction mixture, the resultant was washed twice with water and once with saturated brine, and then dried over anhydrous sodium sulfate, and the solvent was then distilled off under reduced pressure. The residue was purified by silica gel column chromatography (ethyl acetate/hexane) to afford the title compound (230 mg).
$^1$H NMR (500 MHz, CDCl$_3$) δ 0.85-0.93 (9H, m), 1.22-1.36 (40H, m), 1.58-1.65 (6H, m), 1.99-2.05 (8H, m), 2.32 (6H, t, J=7.6 Hz), 2.52 (1H, t, J=7.1 Hz), 3.48 (2H, d, J=6.9 Hz), 4.09-4.14 (6H, m), 5.31-5.38 (4H, m)

C) 2-(((4-(Dimethylamino)butanoyl)oxy)methyl)-2-((dodecanoyloxy)methyl)propane-1,3-diyl(9Z,9'Z) bis-tetradec-9-enoate To a solution of 2-((dodecanoyloxy)methyl)-2-(hydroxymethyl)propane-1,3-diyl (9Z,9'Z)bis-tetradec-9-enoate (230 mg), DMAP (38 mg) and 4-(dimethylamino)butyric acid hydrochloride (105 mg) in DMF (4 mL), 1-ethyl-3-(3-dimethylaminopropyl)carbodiimide hydrochloride (150 mg) was added at room temperature. After stirring for 3 hours, ethyl acetate was added to the reaction mixture, the resultant was washed twice with water and once with saturated brine, and then dried over anhydrous sodium sulfate, and the solvent was then distilled off under reduced pressure. The residue was purified by silica gel column chromatography (NH, ethyl acetate/hexane) to afford the title compound (100 mg).
$^1$H NMR (500 MHz, CDCl$_3$) δ 0.85-0.93 (9H, m), 1.23-1.35 (40H, m), 1.55-1.67 (6H, m), 1.77 (2H, m), 1.98-2.05 (8H, m), 2.20 (6H, s), 2.24-2.33 (8H, m), 2.36 (2H, t, J=7.6 Hz), 4.09-4.13 (8H, m), 5.31-5.38 (4H, m)

Examples 2 and 3, 5 to 7, and 9 and 10 in a table below were produced in accordance with any of the methods shown in Examples above and methods conforming thereto.

Table 1 shows compound names, structures, and mass numbers observed in production (indicated as MS in the table) for those Examples together with Examples 1, 4, 8, and 11.

TABLE 1

| Example number | IUPAC name | Structural formula | MS: m/z (M + H) |
|---|---|---|---|
| 1 | 3-((4-(dimethylamino)butanoyl)oxy)-2,2-bis(((9Z)-tetradec-9-enoyloxy)methyl)propyl (9Z)-tetradec-9-enoate | | 874.75 |
| 2 | 3-((5-(dimethylamino)pentanoyl)oxy)-2,2-bis(((9Z)-tetradec-9-enoyloxy)methyl)propyl (9Z)-tetradec-9-enoate | | 888.73 |
| 3 | 3-((6-(dimethylamino)hexanoyl)oxy)-2,2-bis(((9Z)-tetradec-9-enoyloxy)methyl)propyl (9Z)-tetradec-9-enoate | | 902.74 |
| 4 | 3-((4-(dimethylamino)butanoyl)oxy)-2,2-bis(((9Z)-tetradec-9-enoyloxy)methyl)propyl (9Z)-hexadec-9-enoate | | 902.74 |
| 5 | 3-((5-(dimethylamino)pentanoyl)oxy)-2,2-bis(((9Z)-tetradec-9-enoyloxy)methyl)propyl (9Z)-hexadec-9-enoate | | 916.76 |
| 6 | 3-((5-(dimethylamino)pentanoyl)oxy)-2,2-bis(((9Z)-tetradec-9-enoyloxy)methyl)propyl (9Z)-octadec-9-enoate | | 944.79 |

TABLE 1-continued

| Example number | IUPAC name | Structural formula | MS: m/z (M + H) |
|---|---|---|---|
| 7 | 3-((5-(dimethylamino)pentanoyl)oxy)-2,2-bis(((9Z)-tetradec-9-enoyloxy)methyl)propyl (9Z,12Z)-octadec-9,12-dienoate | | 942.77 |
| 8 | 2-(((N,N-dimethyl-β-alanyl)oxy]methyl}-2-[(octanoyloxy)methyl)propane-1,3-diyl (9Z,9'Z)bis-tetradec-9-enoate | | 778.62 |
| 9 | 2-(((4-(dimethylamino)butanoyl)oxy)methyl)-2-((octanoyloxy)methyl)propane-1,3-diyl (9Z,9'Z)bis-tetradec-9-enoate | | 792.63 |
| 10 | 2-((decanoyloxy)methyl)-2-(((4-(dimethylamino)butanoyl)oxy)methyl)propane-1,3-diyl (9Z,9'Z)bis-tetradec-9-enoate | | 820.67 |
| 11 | 2-(((4-(dimethylamino)butanoyl)oxy)methyl)-2-((dodecanoyloxy)methyl)propane-1,3-diyl (9Z,9'Z)bis-tetradec-9-enoate | | 848.70 |

Production Example and Test Example for Composition Containing Lipid Particle of Present Invention and Nucleic Acid for Nucleic Acid Introduction Production Example 1

A lipid mixture (cationic lipid produced in Examples: DPPC:cholesterol:GM-020=60:10.6:28:1.4, in mole ratio) was dissolved in 90% EtOH/10% RNase-free water to afford a 8.5 mg/mL lipid solution. Luciferase mRNA (TriLink Bio Technologies) was dissolved in 10 mM 2-morpholinoethanesulfonate (MES) buffer at pH 4.0 to afford a 0.22 mg/mL nucleic acid solution. The lipid solution and nucleic acid solution obtained were mixed by using the apparatus Nano-Assemblr (Precision Nanosystems) at room temperature with a flow rate ratio of 3 mL/min:6 mL/min to afford a dispersion containing a lipid particle encapsulating the nucleic acid. By using a Slyde-A-Lyzer (molecular weight cutoff: 20k, Thermo Fisher Scientific), the dispersion obtained was dialyzed with water at room temperature for 1 hour and with PBS at 4° C. for 48 hours. Subsequently, filtration was performed with a 0.2 m syringe filter (IWAKI CO., LTD.) to prepare a composition for nucleic acid introduction, and thereafter the composition was stored at 4° C. The particle size of the lipid particle was measured by using a Zetasizer Nano ZS (Malvern Instruments Limited). The mRNA concentration and encapsulation ratio of the lipid particle were measured by using a Quant-iT™ RiboGreen® (Invitrogen). Table 2 shows the analysis results.

TABLE 2

| Cationic lipid | Particle size (nm) | mRNA Concentration (μg/mL) | Encapsulation ratio (%) |
|---|---|---|---|
| Example 1 | 71 | 136 | 96 |
| Example 2 | 90 | 73 | 96 |
| Example 3 | 93 | 87 | 96 |
| Example 4 | 76 | 113 | 97 |
| Example 5 | 91 | 96 | 98 |
| Example 8 | 67 | 84 | 94 |
| Example 9 | 108 | 129 | 62 |
| Example 10 | 92 | 86 | 84 |
| Example 11 | 83 | 85 | 92 |

[Test Example 1] Test of mRNA Transfection into Cultured Cells

The human colorectal cancer-derived cell line HCT116 cells were cultured in a 96-well plate at a cell density of 6000 cells/well, and 24 hours thereafter 10 μL of the composition containing 10 ng of luciferase mRNA for nucleic acid introduction (a solution obtained by diluting the product of Production Example 1 to an mRNA concentration of 10 ng/10 μL) was added to the medium. The level of luciferase expressed in HCT116 24 hours after the addition of mRNA was measured by using a Picagene LT2.0 kit (TOYOBO CO., LTD.). Tables 3 and 4 show the measurement results.

TABLE 3

| Cationic lipid | Mean value of luminescence (cps) for 3 wells |
|---|---|
| PBS Control | 560 |
| Example 1 | 227720 |
| Example 2 | 570027 |
| Example 3 | 412187 |
| Example 4 | 407547 |
| Example 5 | 545507 |
| Example 8 | 3853 |
| Example 10 | 1203467 |
| Example 11 | 953520 |

TABLE 4

| Cationic lipid | Mean value of luminescence (cps) for 3 wells |
|---|---|
| PBS Control | 627 |
| Example 9 | 549893 |

Production Example and Test Example for Composition Containing Lipid Particle of Present Invention and Nucleic Acid for Nucleic Acid Introduction Production Example 2

A lipid mixture (cationic lipid produced in Examples: DPPC:cholesterol:GM-020=60:10.6:28:1.4, in mole ratio) was dissolved in 90% EtOH/10% RNase-free water to afford an approximately 7 mg/mL lipid solution. Equal amounts of an siRNA for Col1a1 and an siRNA for Factor VII (FVII) were mixed together, and the mixture was dissolved in 25 mM acetate buffer at pH 4.0 to afford a 0.2 mg/mL nucleic acid solution. Sequence information on the siRNAs are shown in a table below. The lipid solution and nucleic acid solution obtained were mixed by using the apparatus Nano-Assemblr (Precision Nanosystems) at room temperature with a flow rate ratio of 3 mL/min:9 mL/min to afford a dispersion containing a lipid particle including the nucleic acids. By using a Slyde-A-Lyzer (molecular weight cutoff: 20k, Thermo Fisher Scientific), the dispersion obtained was dialyzed with water at room temperature for 1 hour and with PBS at 4° C. for 48 hours. Subsequently, filtration was performed with a 0.2 m syringe filter (IWAKI CO., LTD.) to prepare a composition for nucleic acid introduction, and thereafter the composition was stored at 4° C. The particle size of the lipid particle was measured by using a Zetasizer Nano ZS (Malvern Instruments Limited). The mRNA concentration and encapsulation ratio of the lipid particle were measured by using a Quant-iT™ RiboGreen® (Invitrogen). Table 6 shows the analysis results.

TABLE 5

| Col1a1 siRNA (cited from Calvente et al. Hepatology 2015, 62:4) |
|---|
| Sense 5' - G[mU][mC][mU]AGA[mC]A[mU]G[mU][mU][mC]AG[mC][mU][mU][ts]t - 3' |
| Antisense 5' - AAGCUGAA[mC]AUGUC[mU]AGAC[ts]t - 3' |

| Factor VII siRNA (cited from Landesman et al. Silence 2010, 1:16) |
|---|
| Sense 5' - [mC][mU]A[mC]GAAAG[mC]A[mU][mC][mC][mU][mU][mC]A[mU][ts]t - 3' |
| Antisense 5' - AUGAAGGAUGCUUUCG[mU]AG[ts]t - 3' |

N: RNA
n: DNA
[mN]: 2'-OMe RNA
[ns]: phosphorothioate

TABLE 6

| Compound | Particle size (nm) | siRNA Concentration (µg/ml) | Encapsulation ratio (%) |
|---|---|---|---|
| Example 2 | 104 | 251 | 98 |
| Example 3 | 117 | 196 | 95 |
| Example 10 | 88 | 307 | 90 |
| Example 11 | 85 | 402 | 91 |
| Example 4 | 90 | 355 | 89 |
| Example 5 | 103 | 367 | 94 |
| Example 6 | 87 | 333 | 98 |
| Example 7 | 102 | 320 | 96 |

[Test Example 2] Test of siRNA Delivery to Hepatic Stellate Cells in Model Mice with Liver Disorder Caused by Carbon Tetrachloride The PBS dispersion of the lipid particle including the Col1a1 siRNA and the FVII siRNA was diluted with PBS to respective siRNA concentrations of 40 µg/mL and 120 µg/mL, and administered to the orbital sinus of each Balb/c mouse to achieve respective siRNA doses of 0.2 mg/kg and 0.6 mg/kg. Three hours after the administration of the siRNAs, carbon tetrachloride was orally administered to achieve a dose of 0.1 mL/kg. Four days after the administration of carbon tetrachloride, each mouse was euthanized by bleeding under anesthesia with isoflurane, and the liver was removed. From the liver obtained, the total RNA was extracted with an RNeasy Mini Kit (QIAGEN), and the Col1a1 mRNA, FVII mRNA, and GAPDH mRNA levels were measured through a quantitative PCR method. The expression reduction rates for Col1a1 mRNA and FVII mRNA normalized against the GAPDH mRNA level were calculated with reference to those for mice without siRNA administration, and the following table shows the calculation results.

TABLE 7

| Compound | COL1A1 Knockdown efficiency (%) | FVII Knockdown efficiency (%) |
|---|---|---|
| Example 2 | 73 | 0 |
| Example 3 | 81 | 0 |
| Example 10 | 31 | 0 |
| Example 11 | 60 | 0 |
| Example 4 | 67 | 19 |
| Example 5 | 83 | 14 |
| Example 6 | 86 | 27 |
| Example 7 | 85 | 24 |

INDUSTRIAL APPLICABILITY

The compound, the lipid particle, or the composition of the present invention enables introduction of nucleic acids into various types of cells, tissues, or organs. Accordingly, the compound, the lipid particle, or the composition of the present invention is available as a DDS technique for nucleic acid drugs. In addition, the compound, the lipid particle, or the composition of the present invention is available as a reagent for nucleic acid introduction for research.

The invention claimed is:

1. A compound represented by formula (I):

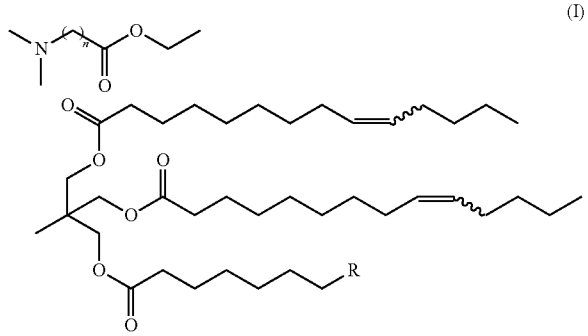

wherein:
n represents an integer of 2 to 5;
R represents a linear $C_{1-5}$ alkyl group, a linear $C_{7-11}$ alkenyl group, or a linear $C_{11}$ alkadienyl group; and
wavy lines each independently represent a cis-bond or a trans-bond, or a salt thereof.

2. 3-((4-(Dimethylamino)butanoyl)oxy)-2,2-bis(((9Z)-tetradec-9-enoyloxy)methyl)propyl (9Z)-tetradec-9-enoate or a salt thereof.

3. 3-((5-(Dimethylamino)pentanoyl)oxy)-2,2-bis(((9Z)-tetradec-9-enoyloxy)methyl)propyl (9Z)-tetradec-9-enoate or a salt thereof.

4. 3-((6-(Dimethylamino)hexanoyl)oxy)-2,2-bis(((9Z)-tetradec-9-enoyloxy)methyl)propyl (9Z)-tetradec-9-enoate or a salt thereof.

5. A lipid particle comprising the compound or a salt thereof according to claim 1.

6. A composition for nucleic acid introduction comprising a nucleic acid and the lipid particle according to claim 5.

7. The composition according to claim 6, wherein the nucleic acid is an RNA.

8. The composition according to claim 7, wherein the RNA is an mRNA or an siRNA.

* * * * *

UNITED STATES PATENT AND TRADEMARK OFFICE
CERTIFICATE OF CORRECTION

PATENT NO. : 11,993,570 B2
APPLICATION NO. : 17/900412
DATED : May 28, 2024
INVENTOR(S) : Satoru Matsumoto et al.

Page 1 of 1

It is certified that error appears in the above-identified patent and that said Letters Patent is hereby corrected as shown below:

In the Claims

In Column 45, Claim 1, Line 35, please replace:

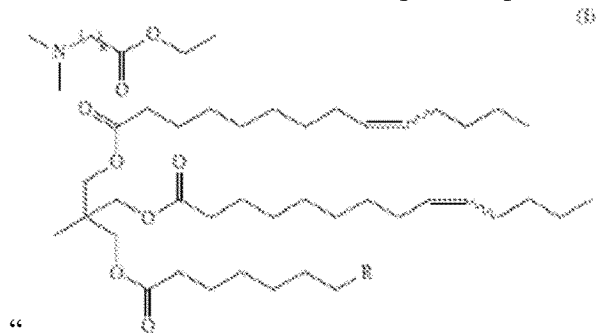

"                                                                                "

With:

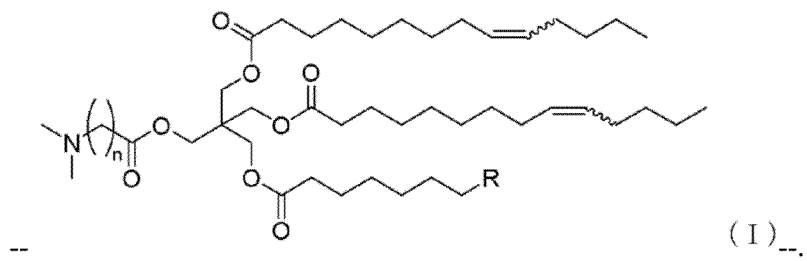

-- (I) --.

Signed and Sealed this
Twenty-ninth Day of October, 2024

Katherine Kelly Vidal
*Director of the United States Patent and Trademark Office*

SEQUENCE LISTING

```
Sequence total quantity: 4
SEQ ID NO: 1            moltype = RNA  length = 21
FEATURE                 Location/Qualifiers
modified_base           20..21
                        mod_base = OTHER
                        note = thymine
misc_feature            1..21
                        note = Col1a1 siRNA (Sense)
misc_feature            1..21
                        note = The sequence comprises both RNA and DNA bases, some
                         of which are modified bases.
modified_base           2
                        mod_base = OTHER
                        note = The "u" stands for 2'-O-methyluridine (um)
modified_base           3
                        mod_base = OTHER
                        note = The "c" stands for 2'-O-methylcytidine (cm)
modified_base           4
                        mod_base = OTHER
                        note = The "u" stands for 2'-O-methyluridine (um)
modified_base           8
                        mod_base = OTHER
                        note = The "c" stands for 2'-O-methylcytidine (cm)
modified_base           10
                        mod_base = OTHER
                        note = The "u" stands for 2'-O-methyluridine (um)
modified_base           12
                        mod_base = OTHER
                        note = The "u" stands for 2'-O-methyluridine (um)
modified_base           12
                        mod_base = OTHER
                        note = The "c" stands for 2'-O-methylcytidine (cm)
modified_base           13
                        mod_base = OTHER
                        note = The "u" stands for 2'-O-methyluridine (um)
modified_base           14
                        mod_base = OTHER
                        note = The "c" stands for 2'-O-methylcytidine (cm)
modified_base           17
                        mod_base = OTHER
```

```
                             note = The "c" stands for 2'-O-methylcytidine (cm)
modified_base                18
                             mod_base = OTHER
                             note = The "u" stands for 2'-O-methyluridine (um)
modified_base                20..21
                             mod_base = OTHER
                             note = The nucleosides (t and t) are bound with
                              phosphorothioate.
source                       1..21
                             mol_type = other RNA
                             organism = synthetic construct
SEQUENCE: 1
gtctagacat gttcagcttt t                                                   21

SEQ ID NO: 2                 moltype = RNA  length = 21
FEATURE                      Location/Qualifiers
modified_base                20..21
                             mod_base = OTHER
                             note = thymine
misc_feature                 1..21
                             note = Col1a1 siRNA (Antisense)
misc_feature                 1..21
                             note = The sequence comprises both RNA and DNA bases, some
                              of which are modified bases.
modified_base                9
                             mod_base = OTHER
                             note = The "c" stands for 2'-O-methylcytidine (cm)
modified_base                15
                             mod_base = OTHER
                             note = The "u" stands for 2'-O-methyluridine (um)
modified_base                20..21
                             mod_base = OTHER
                             note = The nucleosides (t and t) are bound with
                              phosphorothioate.
source                       1..21
                             mol_type = other RNA
                             organism = synthetic construct
SEQUENCE: 2
aagctgaaca tgtctagact t                                                   21

SEQ ID NO: 3                 moltype = RNA  length = 21
FEATURE                      Location/Qualifiers
modified_base                20..21
                             mod_base = OTHER
                             note = thymine
misc_feature                 1..21
                             note = Factor VII siRNA (Sense)
misc_feature                 1..21
                             note = The sequence comprises both RNA and DNA bases, some
                              of which are modified bases.
modified_base                1
                             mod_base = OTHER
                             note = The "c" stands for 2'-O-methylcytidine (cm)
modified_base                2
                             mod_base = OTHER
                             note = The "u" stands for 2'-O-methyluridine (um)
modified_base                4
                             mod_base = OTHER
                             note = The "c" stands for 2'-O-methylcytidine (cm)
modified_base                10
                             mod_base = OTHER
                             note = The "c" stands for 2'-O-methylcytidine (cm)
modified_base                12
                             mod_base = OTHER
                             note = The "u" stands for 2'-O-methyluridine (um)
modified_base                13
                             mod_base = OTHER
                             note = The "c" stands for 2'-O-methylcytidine (cm)
modified_base                14
                             mod_base = OTHER
                             note = The "c" stands for 2'-O-methylcytidine (cm)
modified_base                15
                             mod_base = OTHER
                             note = The "u" stands for 2'-O-methyluridine (um)
modified_base                16
                             mod_base = OTHER
                             note = The "u" stands for 2'-O-methyluridine (um)
modified_base                17
                             mod_base = OTHER
```

```
                        note = The "c" stands for 2'-O-methylcytidine (cm)
modified_base           19
                        mod_base = OTHER
                        note = The "u" stands for 2'-O-methyluridine (um)
modified_base           20..21
                        mod_base = OTHER
                        note = The nucleosides (t and t) are bound with
                         phosphorothioate.
source                  1..21
                        mol_type = other RNA
                        organism = synthetic construct
SEQUENCE: 3
ctacgaaagc atccttcatt t                                                  21

SEQ ID NO: 4            moltype = RNA  length = 21
FEATURE                 Location/Qualifiers
misc_feature            1..21
                        note = Factor VII siRNA (Antisense)
misc_feature            1..21
                        note = The sequence comprises both RNA and DNA bases, some
                         of which are modified bases.
modified_base           17
                        mod_base = OTHER
                        note = The "u" stands for 2'-O-methyluridine (um)
modified_base           20..21
                        mod_base = OTHER
                        note = The nucleosides (t and t) are bound with
                         phosphorothioate.
source                  1..21
                        mol_type = other RNA
                        organism = synthetic construct
modified_base           20..21
                        mod_base = OTHER
                        note = thymine
SEQUENCE: 4
atgaaggatg ctttcgtagt t                                                  21
```